United States Patent
Niazi et al.

(10) Patent No.: US 12,329,809 B2
(45) Date of Patent: *Jun. 17, 2025

(54) CELLULAR ADJUVANTS FOR VIRAL INFECTION

(71) Applicant: NantBio, Inc., Culver City, CA (US)

(72) Inventors: Kayvan Niazi, Culver City, CA (US); Raymond Wong, Los Angeles, CA (US); Peter Sieling, Culver City, CA (US); Philip T. Liu, Culver City, CA (US)

(73) Assignee: NantBio, Inc., Culver City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/664,120

(22) Filed: May 14, 2024

(65) Prior Publication Data

US 2024/0299521 A1    Sep. 12, 2024

Related U.S. Application Data

(63) Continuation of application No. 17/684,121, filed on Mar. 1, 2022, now Pat. No. 12,220,452, which is a continuation of application No. 16/536,962, filed on Aug. 9, 2019, now Pat. No. 11,298,414.

(60) Provisional application No. 62/717,560, filed on Aug. 10, 2018.

(51) Int. Cl.
| | |
|---|---|
| *A61K 39/02* | (2006.01) |
| *A61K 39/00* | (2006.01) |
| *A61K 39/108* | (2006.01) |
| *C12N 15/861* | (2006.01) |
| *A61K 9/00* | (2006.01) |

(52) U.S. Cl.
CPC ...... *A61K 39/0258* (2013.01); *A61K 39/0002* (2013.01); *C12N 15/861* (2013.01); *A61K 9/0019* (2013.01); *A61K 2039/605* (2013.01); *C12N 2770/16034* (2013.01)

(58) Field of Classification Search
CPC ............. A61K 39/07; A61K 39/0258; A61K 39/0002; A61K 2039/605; C12N 15/861; C12N 2770/16034
See application file for complete search history.

(56) References Cited

U.S. PATENT DOCUMENTS

| | | | |
|---|---|---|---|
| 6,121,043 A | 9/2000 | Cochran et al. | |
| 6,238,914 B1 | 5/2001 | Boyce | |
| 11,298,414 B2 * | 4/2022 | Niazi ................... | C12N 15/861 |
| 2016/0058852 A1 | 3/2016 | Ter Meulen et al. | |
| 2022/0370587 A1 | 11/2022 | Niazi et al. | |

FOREIGN PATENT DOCUMENTS

| | | |
|---|---|---|
| CN | 101321781 A | 12/2008 |
| CN | 108135991 A | 6/2018 |
| CN | 108367061 A | 8/2018 |
| WO | 2007/062656 A2 | 6/2007 |
| WO | 2013/090806 A2 | 6/2013 |
| WO | 2017/017049 A1 | 2/2017 |

OTHER PUBLICATIONS

Badr El-Din, NK et al. "Baker's Yeast Sensitizes Metastatic Breast Cancer Cells to Paclitaxel In Vitro. Integrative cancer therapies", Jun. 2018, Epub Nov. 21, 2017, vol. 17, No. 2, 19/18/14-15 pp. 542-550.
International Search Report and Written Opinion received for PCT Application Serial No. PCT/US2019/045977 dated Oct. 22, 2019, 12 pages.
Liu, Q et al., "Construction of *Escherichia coli* Mutant with Decreased Endotoxic Activity by Modifying Lipid A Structure", Marine Drugs, Mar. 27, 2015, vol. 13, No. 6, pp. 3388-3406.
International Preliminary Report on Patentability Chapter I received for International PCT Application Serial No. PCT/US2019/045977 dated Feb. 25, 2021, 11 pages.
Communication pursuant to Rule 164(1) EPC received for European Patent Application Serial No. 19847366.2 dated Sep. 6, 2021, 17 Pages.
Andrieu et al., "Mucosal Siv Vaccines 1-15 Comprising Inactivated Virus Particles And Bacterial Adjuvants Induce CD8+ T-Regulatory Cells That Suppress SIV-Positive Cd4+ T-Cell Activation And Prevent Siv Infection In The Macaque Model", Frontiers In Immunology, 2014, vol. 5, No. 297, 11 Pages.
Xiao et al., "Flagellin FljB as an adjuvant to the recombinant adenovirus rabies glycoprotein vaccine increases mmune responses against rabies in mice", Archives Of Virology, 2017, vol. 162, pp. 2655-2665.
Krzykawski et al., "Combined Bacterial And Viral Treatment: A Novel Anti Cancer Strategy", Central European Journal Of Immunology, 2015, vol. 40, No. 3, pp. 366-372.
Crompton et al., "Expression of A Foreign Epitope On The Surface of The Adenovirus Hexon", Journal Of General Virology, 1994, vol. 75, pp. 133-139.
Extended European Search Report received for European Patent Application Serial No. 1984 7366 .2 dated Dec. 7, 2021, 13 pages.
Non-Final Office Action received for U.S. Appl. No. 16/536,962 dated Oct. 8, 2020, 35 pages.
Final Office Action received for U.S. Appl. No. 16/536,962 dated Feb. 23, 2021, 27 pages.
Non-Final Office Action received for U.S. Appl. No. 16/536,962 dated May 14, 2021, 14 pages.
Final Office Action received for U.S. Appl. No. 16/536,962 dated Aug. 19, 2021, 21 pages.

(Continued)

*Primary Examiner* — Mary Maille Lyons
(74) *Attorney, Agent, or Firm* — Umberg Zipser LLP

(57) ABSTRACT

Two-component vaccine formulations and methods are contemplated where the vaccine has an adjuvant component and a therapeutic component. The therapeutic component comprises preferably a recombinant therapeutic virus encoding a therapeutic antigen while the adjuvant component comprises a non-host cell or immune stimulating portion thereof. Notably, use of the adjuvant component will result in significant uptake of the therapeutic component into immune competent cells, even in the absence of receptors for entry of the therapeutic component. In addition, such adjuvant also stimulates expression of the therapeutic antigen.

18 Claims, 19 Drawing Sheets

(56) References Cited

OTHER PUBLICATIONS

Notice of Allowance received for U.S. Appl. No. 16/536,962 dated Feb. 2, 2022, 30 pages.
Notification of Grant of Patent Right received for CN Application No. 201980031529.0 dated Jan. 2, 2024, 04 pages (including English Translation).
Office Action received for CN Application No. 201980031529.0 dated Apr. 8, 2023, 24 pages (including English Translation).
Office Action received for CN Application No. 201980031529.0 dated Aug. 24, 2023, 16 pages (including English Translation).
Rao, et al., "IL-12 Is an Effective Adjuvant to Recombinant Vaccinia Virus-Based Tumor Vaccines", J Immunol. May 1, 1996; 156(9): 3357-3365.

* cited by examiner

CELLULAR ADJUVANTS FOR VIRAL INFECTION

This application is a continuation of U.S. patent application Ser. No. 17/684,121, filed Mar. 1, 2022, which is a continuation of U.S. Pat. No. 11,298,414 with Ser. No. 16/536,962, filed Aug. 9, 2019, which claims priority to U.S. Provisional Application with the Ser. No. 62/717,560, which was filed Aug. 10, 2018.

FIELD OF THE INVENTION

The field of the invention is compositions and methods of improved virus-based immune therapeutics, especially as it relates to improvements in infection and expression of recombinant viral nucleic acids, for example, in cancer therapy.

BACKGROUND OF THE INVENTION

The background description includes information that may be useful in understanding the present invention. It is not an admission that any of the information provided herein is prior art or relevant to the presently claimed invention, or that any publication specifically or implicitly referenced is prior art.

All publications and patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Vaccinations are common and well known in the art to treat or prevent disease, and/or to generate antibodies or antigen reactive immune competent cells. In most cases, vaccination is performed using an adjuvant that will assist in stimulation of an immune reaction. For example, small molecule or inorganic adjuvants include various aluminum salts, various simple oils such as paraffin or squalene, and more complex compounds such as saponins and cytokines. Certain adjuvants can also be significantly more complex, and such adjuvants include killed bacteria (e.g., *Mycobacterium bovis, Bordetella pertussis*, etc.), in some cases formulated as Freund's adjuvant (i.e., water-in-oil emulsion with killed *Mycobacterium tuberculosis*). In general, and in most cases, adjuvants are used to potentiate an immune reaction against a single antigen (e.g., where antibody production is desired) or a typically inactivated pathogen (e.g., where therapeutic immunity is desired).

Therefore, where neutralizing activity against an antigen is desired, adjuvants are often beneficial. However, where immunization is performed using recombinant viral particles that trigger antigen production within a cell infected by the recombinant virus, an immune reaction against the recombinant viral particles is not desired, and as such, use of adjuvants would not be deemed advantageous. Moreover, in most immunotherapies using recombinant viral particles the antigenic protein is produced within a cell and as such not 'combinable' with an adjuvant.

To boost effectiveness of immunotherapy using recombinant viral particles, IL-12 was proposed as a potentiating agent (e.g., *J Immunol.* 1996; 156(9): 3357-3365). However, IL-12 may not always be well tolerated, and may also skew an immune response. In still other known approaches, IL15 is co-expressed from the recombinant viral genome (e.g., WO 2017/139725). While such approach is often beneficial to stimulate an immune response in the context of an expressed antigen, the desired activity of IL-15 is dependent on viral uptake and expression of the recombinant IL-15 gene in the first place.

Thus, even though multiple methods of boosting an immune response are known in the art, all or almost all of them suffer from various disadvantages, especially where the immune response is against antigens encoded in a recombinant virus. Consequently, there is still a need to provide improved compositions and methods that increase likelihood of a therapeutic response in immune therapy using recombinant viral particles.

SUMMARY OF THE INVENTION

The inventive subject matter is directed to various immune therapeutic compositions and methods, and especially cell-based adjuvants for recombinant viral expression systems, in which the cell-based adjuvant increases infectivity of the virus and expressivity of the recombinant payload.

In one aspect of the inventive subject matter, the inventor contemplates a method of increasing expression of a recombinant antigen in a host cell. Particularly preferred methods will include a step of providing a virus having a viral genome that includes in the viral genome a recombinant sequence encoding an antigen, wherein the sequence is operably linked to a promoter to drive expression of the antigen in a host cell; another step of providing a non-host cell or immune stimulating portion thereof; and a further step of concurrently exposing the host cell with the virus and the non-host cell or immune stimulating portion thereof under conditions to allow uptake of the virus into the cell and to allow for expression of the recombinant sequence.

For example, suitable non-host cells will typically belong to a species other than the host cell species, and will in some embodiments be a pathogenic non-host cell, or a bacterial cell (e.g., ΔLPS-*E. coli*), or a yeast cell (*S. cerevisiae*). In other examples, the immune stimulating portion of the non-host cell will include a pathogen-associated molecular pattern (PAMP) protein and/or a damage-associated molecular pattern (DAMP) protein. Viewed from a different perspective, the immune stimulating portion may also include a toll-like receptor (TLR) ligand and/or a pattern recognition receptor (PRR) ligand. Contemplated viruses include an adenovirus (e.g., Ad5[E1-, E2b-] virus) or a coxsackie virus, and the antigen will typically include a patient and tumor specific neoepitope and/or a tumor associated antigen. In further embodiments, the step of concurrently exposing is performed in vivo, typically using a vaccine composition that comprises the virus and the non-host cell or immune stimulating portion thereof.

Therefore, in another aspect of the inventive subject matter, the inventors contemplate a method of treating a patient using an immune therapy. Most typically such method includes a step of administering a two-component vaccine formulation to the patient, wherein the vaccine formulation has an adjuvant component and a therapeutic component. Preferred therapeutic components comprise a virus having a viral genome that includes in the viral genome a recombinant sequence encoding an antigen, wherein the sequence is operably linked to a promoter to drive expression of the antigen in a cell of the patient; and preferred adjuvant components comprise a non-host cell or immune stimulating portion thereof. With respect to the non-host cell, the immune stimulating portion, the virus, and the antigen, the same considerations as noted above apply.

In yet another aspect of the inventive subject matter, the inventors contemplate a method of transfecting a virus into an immune competent cell lacking a receptor for entry of the virus into the cell. Such method will typically include a step of concurrently exposing the immune competent cell with the virus and a non-host cell or immune stimulating portion thereof under conditions to allow uptake of the virus into the cell. Preferably, the virus has a viral genome that includes a recombinant sequence encoding an antigen, wherein the sequence is operably linked to a promoter to drive expression of the antigen in the immune competent cell, and the non-host cell or immune stimulating portion thereof is a bacterium (e.g., ΔLPS-*E. coli*) or a yeast cell (e.g., *S. cerevisiae*).

For example, suitable immune competent cells include dendritic cells, macrophages, and B lymphocyte. Contemplated viruses include adenovirus (e.g., Ad5[E1-, E2b-] virus) and coxsackie virus, while the receptor is a CXADR receptor. Moreover, it is generally preferred that the step of concurrently exposing is performed in vivo, typically by using a vaccine composition comprising the virus and the non-host cell or immune stimulating portion thereof. With respect to the immune stimulating portion, the same considerations as provided above apply.

Consequently, the inventors also contemplate a vaccine composition that comprises an adjuvant component and a therapeutic component, wherein the therapeutic component comprises a virus having a viral genome that includes in the viral genome a recombinant sequence encoding an antigen, wherein the sequence is operably linked to a promoter to drive expression of the antigen in a cell of the patient, and wherein the adjuvant component comprises a non-host cell or immune stimulating portion thereof. With respect to the non-host cell, the immune stimulating portion, the virus, and the antigen, the same considerations as noted above apply. Among other uses, the inventors especially contemplate the use of such vaccine compositions in the treatment of cancer or an infectious disease.

Various objects, features, aspects and advantages of the inventive subject matter will become more apparent from the following detailed description of preferred embodiments, along with the accompanying drawing in which like numerals represent like components.

DETAILED DESCRIPTION

Figure 1:
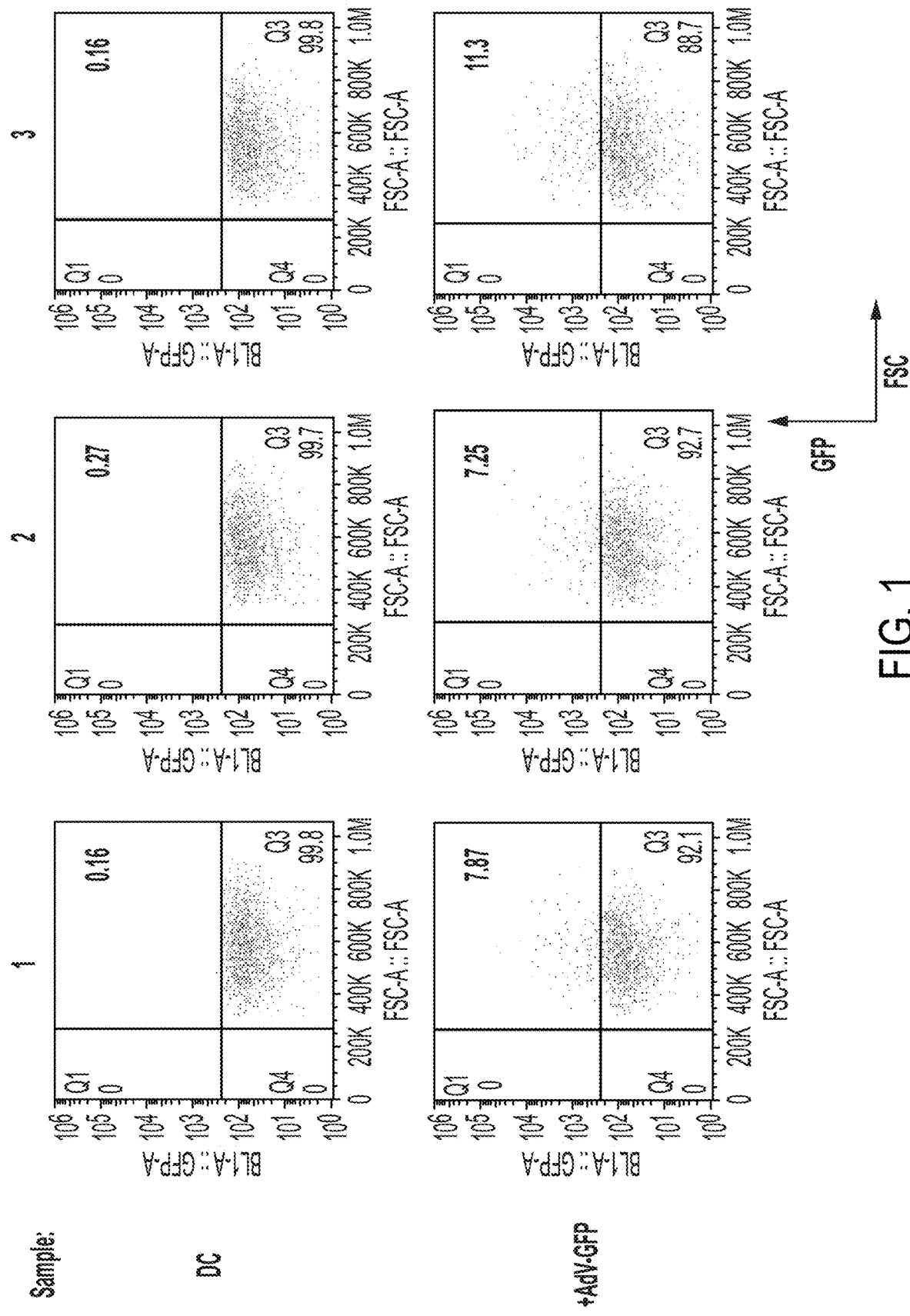
FIG. 1 depicts exemplary results for co-incubation of adenovirus with ΔLPS-*E. coli* indicating an improved AdV uptake and cargo expression.
Figure 1:
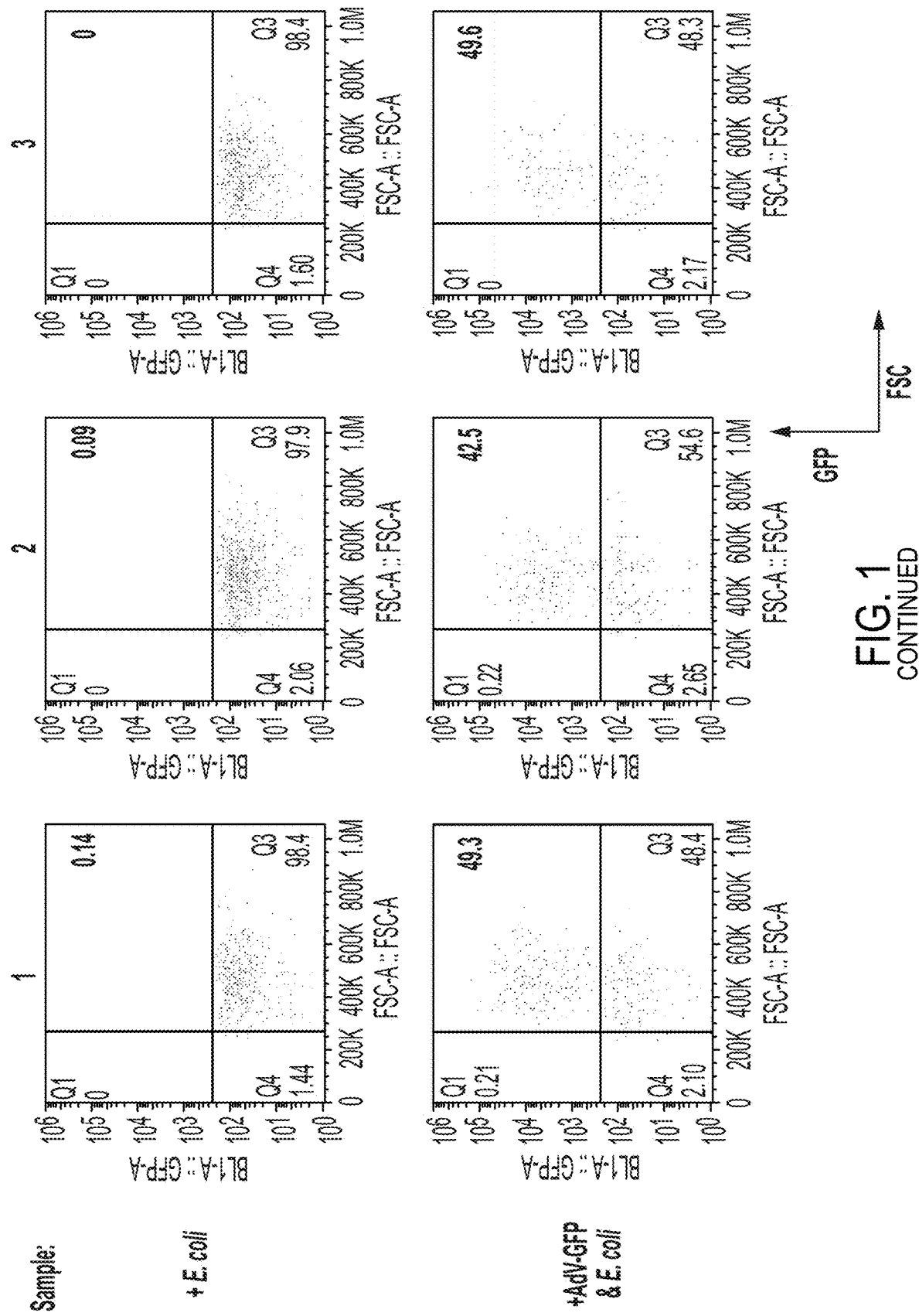

The inventors have discovered that administration of a viral vaccine composition can be complemented with a cell-based adjuvant to so increase viral uptake into a variety of cells, and particularly immune competent cells (even where such cells lack a receptor for viral entry such as a CXADR) and/or to increase expression levels of recombinant genes carried by the virus. Notably, the increase in viral uptake and expression levels of recombinant genes carried by the virus could be observed in a variety of cell-based adjuvants, particularly where the cells in the cell-based adjuvant are different from the cells that are to be transfected.

For example, for a recombinant viral vaccine (i.e., virus encoding a recombinant antigen) to be effective, professional antigen presenting cells or immune competent cells such as dendritic cells, B lymphocytes, or macrophages first must take up the virus and its recombinant nucleic acid, and then efficiently express and process the recombinant antigen prior to presentation to antigen-specific T cells to so induce a desired immune response and immunological memory. Among other viruses, Adenovirus subgroup C type 5 is frequently used for recombinant viral vaccines. However, adenovirus has a primary tropism for cells that express the CXADR protein (coxsackievirus and adenovirus receptor). Unlike many epithelial cells, antigen presenting cells typically do not express CXADR, greatly inhibiting the efficiency of gene transfer into this type of cells.

The inventors now discovered that the use of cell-based adjuvants such as bacteria and/or yeast cells, and immune stimulating portion thereof, can significantly activate antigen presenting cells in a manner that improves (AdV type 5) gene transfer, increases the number of cells that are transduced, and that augments the degree of cargo gene expression on a cell-by-cell basis. Quite unexpectedly, use of such cell-based adjuvants did not result in an increased degradation of the virus and/or expressed antigens, but rather resulted in amplified viral uptake and expression of viral nucleic acid.

With respect to suitable viruses it is contemplated that, among other viruses, preferred viruses are genetically modified to contain a recombinant nucleic acid construct that will give rise to expression of a desired protein, and most typically antigenic protein as discussed in more detail below to so help elicit an immune response against the protein. For example, particularly suitable viruses include adenoviruses, adeno-associated viruses, alphaviruses, herpes viruses, lentiviruses, etc. However, adenoviruses are particularly preferred, and it is further preferred that the virus is a replication deficient and/or non-immunogenic virus, which can be accomplished by targeted deletion of selected viral proteins (e.g., E1, E3 proteins in adenovirus). Such desirable properties may be further enhanced by deleting the E2b gene function. Despite the replication deficiency, high titers of such recombinant viruses can be achieved using genetically modified human 293 cells as has been reported elsewhere (e.g., *J Virol.* 1998 February; 72(2): 926-933). Thus, it should be appreciated that all viruses are deemed suitable for use herein, and particularly those used for gene therapy or immune therapy.

Alternatively, immune therapy need not rely on a virus but may be effected with nucleic acid transfection or vaccination using RNA or DNA, or other recombinant vector that leads to the expression of the neoepitopes (e.g., as single peptides, tandem mini-gene, etc.) in desired cells, and especially immune competent cells. Consequently, contemplated methods may also apply to transfection of host cells with non-enveloped viruses and even naked DNA or RNA as is known from DNA or RNA vaccinations.

Consequently, it should be appreciated that genetically modified viruses will include at least one recombinant sequence element that, when expressed in a host cell, will provide one or more typically immunogenic antigens (antigenic oligo- or polypeptide) to thereby provide a therapeutic effect. For example, as is described in more detail below, a recombinant nucleic acid may be constructed that includes one or more expression cassettes for expression of bacterial or viral antigens, tumor associated antigens, or patient- and tumor specific neoepitopes. In addition, contemplated recombinant nucleic acids may also include an expression cassette that encodes one or more polypeptide or protein adjuvants. With respect to the recombinant immunogenic antigens, it is generally preferred that the antigens are engineered in a manner that directs the antigens towards MHC-I and/or MHC-II presentation. Additionally, or alternatively, it should be noted that the antigenic polypeptide or protein can be expressed as a membrane-bound protein or as a soluble secreted protein.

Therefore, in exemplary aspects of the inventive subject matter, a cancer immune therapy may use a recombinant adenovirus that has as payload (e.g., cancer epitopes or TAA) and further optional functional elements as discussed in more detail below. However, in preferred aspects, the cancer epitopes are tumor- and patient-specific neoepitopes that are filtered according to one or more criteria (e.g., by strength of expression in the tumor, by ability to be presented in a MHC-I or MHC-II complex, etc.).

In this context it should be recognized that neoepitopes can be characterized as expressed random mutations in tumor cells that created unique and tumor specific antigens. Therefore, and viewed from a different perspective, neoepitopes may be identified by considering the type (e.g., deletion, insertion, transversion, transition, translocation) and impact of the mutation (e.g., non-sense, missense, frame shift, etc.), which may as such serve as a content filter through which silent and other non-relevant (e.g., non-expressed) mutations are eliminated. It should also be appreciated that neoepitope sequences can be defined as sequence stretches with relatively short length (e.g., 8-12 mers or 14-20 mers) wherein such stretches will include the change(s) in the amino acid sequences. Most typically, but not necessarily, the changed amino acid will be at or near the central amino acid position. For example, a typical neoepitope may have the structure of $A_4$-N-$A_4$, or $A_3$-N-$A_5$, or $A_2$-N-$A_7$, or $A_5$-N-$A_3$, or $A_7$-N-$A_2$, where A is a proteinogenic wild type or normal (i.e., from corresponding healthy tissue of the same patient) amino acid and N is a changed amino acid (relative to wild type or relative to matched normal). Therefore, the neoepitope sequences contemplated herein include sequence stretches with relatively short length (e.g., 5-30 mers, more typically 8-12 mers, or 14-20 mers) wherein such stretches include the change(s) in the amino acid sequences. Where desired, additional amino acids may be placed upstream or downstream of the changed amino acid, for example, to allow for additional antigen processing in the various compartments (e.g., for proteasome processing in the cytosol, or specific protease processing in the endosomal and/or lysosomal compartments) of a cell.

Identification or discovery of treatment relevant neoepitopes can be performed by various methods known in the art. Most typically, however, computational analysis of the sequence data (e.g., tumor versus matched normal) of a patient tumor will be performed. In preferred methods, such computations analysis is performed in silico by location-guided synchronous alignment of tumor and normal samples as disclosed in US 2012/0059670 and US 2012/0066001 using BAM files and BAM servers. Such analysis advantageously reduces false positive neoepitopes and significantly reduces demands on memory and computational resources. Viewed from another perspective, a patient- and cancer-specific in silico collection of sequences can be established that encode neoepitopes having a predetermined length of, for example, between 5 and 25 amino acids and include at least one changed amino acid. Such collection will typically include for each changed amino acid at least two, at least three, at least four, at least five, or at least six members in which the position of the changed amino acid is not identical. Such collection advantageously increases potential candidate molecules suitable for immune therapy and can then be used for further filtering (e.g., by sub-cellular location, transcription/expression level, MHC-I and/or II affinity, etc.).

In still further contemplated aspects of the inventive subject matter, it should be noted that the neoepitopes/polytopes can be directed towards a specific sub-cellular compartment (e.g., cytosol, endosome, lysosome), and with that, towards a particular MHC presentation type. Such directed expression, processing, and presentation is particularly advantageous as contemplated compositions may be prepared that direct an immune response towards a $CD8^+$ type response (where the polytope is directed to the cytoplasmic space) or towards a $CD4^+$ type response (where the polytope is directed to the endosomal/lysosomal compartment). Moreover, it should be recognized that polytopes that would ordinarily be presented via the MHC-I pathway can be presented via the MHC-II pathway (and thereby mimic cross-presentation of neoepitopes). Therefore, it should be appreciated that neoepitope and polytope sequences may be designed and directed to one or both MHC presentation pathways using suitable sequence elements. With respect to routing the so expressed neoepitopes to the desired MHC-system, it is noted that the MHC-I presented peptides will typically arise from the cytoplasm via proteasome processing and delivery through the endoplasmic reticulum. Thus, expression of the epitopes intended for MHC-I presentation will generally be directed to the cytoplasm as is further discussed in more detail below. On the other hand, MHC-II presented peptides will typically arise from the endosomal and lysosomal compartment via degradation and processing by acidic proteases (e.g., legumain, cathepsin L and cathepsin S) prior to delivery to the cell membrane.

Moreover, it is contemplated that the expression construct (e.g., recombinant viral expression vector or plasmid) may further encode at least one, more typically at least two, even more typically at least three, and most typically at least four co-stimulatory molecules to enhance the interaction between the infected cells (e.g., antigen presenting cells) and T-cells. For example, suitable co-stimulatory molecules include CD80, CD86, CD30, CD40, CD30L, CD40L, ICOS-L, B7-H3, B7-H4, CD70, OX40L, 4-1BBL, while other stimulatory molecules with less defined (or understood) mechanism of action include GITR-L, TIM-3, TIM-4, CD48, CD58, TL1A, ICAM-1, LFA3, and members of the SLAM family. However, especially preferred molecules for coordinated expression with the cancer-associated sequences include CD80 (B7-1), CD86 (B7-2), CD54 (ICAM-1) and CD11 (LFA-1). In addition to co-stimulatory molecules, the inventors also contemplate that one or more cytokines or cytokine analogs may be expressed from the recombinant nucleic acid, and especially preferred cytokines and cytokine analogs include IL-2, IL-15, and IL-a5 superagonist (ALT-803). Moreover, it should be appreciated that expression of the co-stimulatory molecules and/or cytokines will preferably be coordinated such that the neoepitopes or polytope are expressed contemporaneously with one or more co-stimulatory molecules and/or cytokines. Thus, it is typically contemplated that the co-stimulatory molecules and/or cytokines are produced from a single transcript (which may or may not include the sequence portion encoding the polytope), for example, using an internal ribosome entry site or 2A sequence, or from multiple transcripts.

Likewise, it is contemplated that the expression construct may also include a sequence portion that encodes one or more peptide ligands that bind to a checkpoint receptor. Most typically, binding will inhibit or at least reduce signaling via the receptor, and particularly contemplated receptors include CTLA-4 (especially for $CD8^+$ cells), PD-1 (especially for $CD4^+$ cells), TIM1 receptor, 2B4, and CD160. For example, suitable peptide binders can include antibody fragments and especially scFv, but also small molecule peptide ligands (e.g., isolated via RNA display or phage panning) that specifically bind to the receptors. Once more, it should be appreciated that expression of the peptide molecules will preferably be coordinated such that the neoepitopes or polytope are expressed contemporaneously with one or more of the peptide ligands. Thus, it is typically contemplated that the peptide ligands are produced from a single transcript (which may or may not include the sequence portion encoding the polytope), for example, using an internal ribosome entry site or 2A sequence, or from multiple transcripts.

It should be appreciated that all of the above noted co-stimulatory genes and genes coding for inhibitory proteins that interfere with/down-regulate checkpoint inhibition are well known in the art, and sequence information of these genes, isoforms, and variants can be retrieved from various public resources, including sequence data bases accessible at the NCBI, EMBL, GenBank, RefSeq, etc. Moreover, while the above exemplary stimulating molecules are preferably expressed in full length form as expressed in human, modified and non-human forms are also deemed suitable so long as such forms assist in stimulating or activating T-cells. Therefore, muteins, truncated forms and chimeric forms are expressly contemplated herein.

Most typically, the desired nucleic acid sequences for expression from the virus infected cells are under the control of appropriate regulatory elements well known in the art. For example, suitable promoter elements include constitutive strong promoters (e.g., SV40, CMV, UBC, EF1A, PGK, CAGG promoter), but inducible promoters are also deemed suitable for use herein, particularly where induction conditions are typical for a tumor microenvironment. For example, inducible promoters include those sensitive to hypoxia and promoters that are sensitive to TGF-β or IL-8 (e.g., via TRAF, JNK, Erk, or other responsive elements promoter). In other examples, suitable inducible promoters include the tetracycline-inducible promoter, the myxovirus resistance 1 (Mx1) promoter, etc.

Exemplary viral constructs containing antigen sequences and additional functional elements are described in PCT/US18/28889, filed Apr. 23, 2018.

Depending on the particular virus and treatment objective, it should be appreciated that suitable host cells (i.e., cell infected with the recombinant virus or transfected with nucleic acid) may vary considerably. However, it is generally contemplated that the host cells are eukaryotic, and more typically mammalian cells. Where such cells are used for treatment, it is preferred that the host cell is autologous to the recipient or at least HLA compatible (e.g., matching at least 4 digits of at least one HLA-type). On the other hand, suitable host cells will also include non-matched or otherwise allogenic cells, especially where such non-matched or allogenic cells are therapeutic cells (e.g., allogenic stem cells, NK92 cells, etc.). Moreover, it should be noted that the host cells may be part of an existing tissue, be separated from each other, or be cultivated in primary or secondary cell culture.

For example, suitable host cells will include mammalian and especially human cells that are preferably autologous. As noted earlier, it should be recognized that the host cells for viral infection need not have corresponding viral entry proteins (e.g., such as CXADR). Therefore, suitable host cells especially include various blood cells, and especially immune competent cells such as dendritic cell, macrophages, T cells, B cells, monocyte, etc. On the other hand, where the viral infection is performed on a tissue, preferred host cells include various epithelial cells. Consequently, it should be recognized that the host cells may be contacted with the recombinant virus (or recombinant DNA or RNA) in vitro or in vivo.

With respect to suitable non-host cells it is generally contemplated that the non-host cell is a cell that belongs to a species other than the host cell species. However, where the non-host cell is a cell belonging to the same species than the host cell species, it is contemplated that the non-host cell will exhibit one or more stress or danger signals (which may, for example, be done by radiation, exposure to chemotherapeutic agents, etc to trigger expression of NKG2DL, stress markers, pro-apoptotic markers, etc.). Most typically, however, it is contemplated that suitable non-host cells will be bacterial cells and/or yeast cells, which may or may not be pathogenic.

For example, contemplated bacterial cells will include those that are modified to have no or reduced expression of expresses lipopolysaccharides that would otherwise trigger an immune response and cause endotoxic responses, which can lead potentially fatal sepsis (e.g., CD-14 mediated sepsis). Thus, one exemplary bacteria strain with modified lipopolysaccharides includes ClearColi® BL21(DE3) electrocompetent cells. This bacteria strain is BL21 with a genotype F-ompT hsdSB (rB-mB-) gal dem lon λ(DE3 [lacI lacUV5-T7 gene 1 ind1 sam7 nin5]) msbA148 ΔgutQΔkdsD ΔlpxLΔlpxMΔpagPΔlpxPΔeptA. In this context, it should be appreciated that several specific deletion mutations (ΔgutQ ΔkdsD ΔlpxL ΔlpxMΔpagP ΔlpxP ΔeptA) encode the modification of LPS to Lipid $IV_A$, while one additional compensating mutation (msbA148) enables the cells to maintain viability in the presence of the LPS precursor lipid IVA. These mutations result in the deletion of the oligosaccharide chain from the LPS. More specifically, two of the six acyl chains are deleted. The six acyl chains of the LPS are the trigger which is recognized by the Toll-like receptor 4

(TLR4) in complex with myeloid differentiation factor 2 (MD-2), causing activation of NF-κB and production of proinflammatory cytokines. Lipid $IV_A$, which contains only four acyl chains, is not recognized by TLR4 and thus does not trigger the endotoxic response. While electrocompetent BL21 bacteria is provided as an example, the inventors contemplates that the genetically modified bacteria can be also chemically competent bacteria.

Alternatively, the inventors also contemplate that the patient's own endosymbiotic bacteria can be used as a non-host cell. As used herein, the patient's endosymbiotic bacteria refers bacteria residing in the patient's body regardless of the patient's health condition without invoking any substantial immune response. Thus, it is contemplated that the patient's endosymbiotic bacteria is a normal flora of the patient. For example, the patient's endosymbiotic bacteria may include *E. coli* or *Streptococcus* that can be commonly found in human intestine or stomach. In these embodiments, patient's own endosymbiotic bacteria can be obtained from the patient's biopsy samples from a portion of intestine, stomach, oral mucosa, or conjunctiva, or in fecal samples. The patient's endosymbiotic bacteria can then be cultured in vitro and transfected with nucleotides encoding human disease-related antigen(s). In still further contemplated aspects, the bacterial non-host cell may also be a pathogenic cell, including *Bordetella pertussis* and/or *Mycobacterium bovis*. Most typically, but not necessarily, the bacterial non-host cells will be killed before exposure to the host cells.

Similarly, there are numerous yeast strains suitable for use herein, and most typically non-pathogenic yeasts include *Saccharomyces cerevisiae, Saccharomyces boulardi, Pichia pasteuris, Schizosaccharomyces pombe, Candida stellata*, etc. As noted above, such yeast strains may be further genetically modified to reduce one or more adverse traits, and/or to express a recombinant protein that further increases viral infectivity and/or expression. Contemplated yeast strains are typically commercially available and can be modified using protocols well known in the art.

While not limiting the inventive subject matter by any particular theory or hypothesis, the inventors contemplate that one or more components of the non-host cells may act as a danger or damage signal, particularly where the host cells are immune competent cells. Therefore, the inventors not only contemplate use of non-host cells per se, but also one or more immune stimulating portions thereof. Therefore, especially contemplated portions include ligands for PAMP receptors, ligands for DAMP receptors, TLR ligands, CpG, ssDNA, and thapsigargin.

With respect to the ratio between non-host cells to host cells it should be recognized that the exact ratio may vary considerably, depending on the type of host cell, the type of non-host cell (or component thereof), and the virus (or DNA/RNA). However, it is generally preferred that the ratio of host cell to non-host cell is 1:1 to about 1:100, or 1:10 to about 1:1,000, or 1:50 to about 1:5,000, or 1:100 to about 1:10,000, especially where immune competent cells are the host cells and bacterial cells are the non-host cells. Similarly, contemplated ratios of host cell to non-host cell include 100:1 to about 10:1, or 1:1 to about 1:10, or 1:50 to about 1:5.00, or 1:100 to about 1:1,000, especially where immune competent cells are the host cells and yeast cells are the non-host cells.

Exposure of the host cell to the recombinant virus (or DNA/RNA) in the presence of the non-host cell may vary considerably. However, it is generally contemplated that exposure times will be between several minutes and several hours, or between several hours and several days. For example, where the exposure is performed in vitro, exposure times may be between 10 minutes and 2 hours, or between 30 minutes and 4 hours, or between 60 minutes and 6 hours, or between 2 hours and 8 hours, or between 6 hours and 12 hours, or between 12 hours and 24 hours, or between 24 hours and 48, or even longer. On the other hand, where the exposure is performed in vivo (e.g., via vaccine formulation), exposure times may be between 60 minutes and 6 hours, or between 6 hours and 12 hours, or between 12 hours and 24 hours, or between 24 hours and 48, or even longer. In such vaccination scheme, it is typically contemplated that the host cell, the non-host cell, and the recombinant virus (or DNA or RNA) are co-administered in the same formulation.

Consequently, the inventor contemplates various vaccine formulations that are typically formulated for injection or inhalation. Moreover, contemplated vaccine formulations may also include additional adjuvants as discussed further below. Most typically, contemplated vaccine formulations will include a non-host cell (preferably irradiated or otherwise rendered unable to divide or reproduce) and recombinant virus as discussed above. In general, the dosage of the virus may vary considerably, however, it is generally preferred to have at least $10^6$, at least $10^7$, at least $10^8$, at least $10^9$, or at least $10^{10}$ viral particles per vaccine dosage. Likewise, the number of non-host cells may also vary greatly. However, it is generally preferred to have at least $10^{3-5}$, at least $10^{5-7}$, at least $10^{7-9}$, at least $10^{9-11}$, or at least $10^{12}$ non-host cells per vaccine dosage, with higher counts for bacterial non-host cells and lower counts for yeast non-host cells.

With respect to additional adjuvants it is contemplated that all known adjuvants may be used in conjunction with the teachings presented herein. Therefore, contemplated additional adjuvants include various inorganic compounds such as alum, aluminum hydroxide, aluminum phosphate, calcium phosphate hydroxide, mineral oils, and especially paraffin oil. Further suitable adjuvants include small molecule compounds such as squalene, as well as various bacterial products such as killed bacteria *Bordetella pertussis, Mycobacterium bovis* toxoids, etc.

For example, where the recombinant virus includes an adenovirus, and especially AdV with E1 and E2b deleted, it is contemplated that recombinant viruses may combined with *E. coli* clearcoli and formulated into a therapeutic vaccine in a pharmaceutical composition, typically as a sterile injectable composition with a virus titer of between $10^6$-$10^{13}$ virus particles, and more typically between $10^9$-$10^{12}$ virus particles per dosage unit and between $10^5$-$10^7$ bacterial cells, and more typically between $10^6$-$10^{11}$ bacterial cells per dosage unit. Alternatively, virus may be employed to infect patient (or other HLA matched) cells ex vivo in the presence of non-host cells and the so infected cells are then transfused to the patient.

Where desired, additional therapeutic modalities may be employed which may be neoepitope based (e.g., synthetic antibodies against neoepitopes as described in WO 2016/172722), alone or in combination with autologous or allogenic NK cells, and especially haNK cells or taNK cells (e.g., both commercially available from NantKwest, 9920 Jefferson Blvd. Culver City, CA 90232). Where haNK or taNK cells are employed, it is particularly preferred that the haNK cell carries a recombinant antibody on the CD16 variant that binds to a neoepitope of the treated patient, and where taNK cells are employed it is preferred that the chimeric antigen receptor of the taNK cell binds to a neoepitope of the treated patient. The additional treatment modality may also be independent of neoepitopes, and especially preferred modalities include cell-based therapeutics such as activated NK cells (e.g., aNK cells, commercially available from NantKwest, 9920 Jefferson Blvd. Culver City, CA 90232), and non cell-based therapeutics such as chemotherapy and/or radiation. In still further contemplated aspects, immune stimulatory cytokines, and especially IL-2, IL15, and IL-21 may be administered, alone or in combination with one or more checkpoint inhibitors (e.g., ipilimumab, nivolumab, etc.). Similarly, it is still further contemplated that additional pharmaceutical intervention may include administration of one or more drugs that inhibit immune suppressive cells, and especially MDSCs Tregs, and M2 macrophages. Thus, suitable drugs include IL-8 or interferon-γ inhibitors or antibodies binding IL-8 or interferon-γ, as well as drugs that deactivate MDSCs (e.g., NO inhibitors, arginase inhibitors, ROS inhibitors), that block development of or differentiation of cells to MDSCs (e.g., IL-12, VEGF-inhibitors, bisphosphonates), or agents that are toxic to MDSCs (e.g., gemcitabine, cisplatin, 5-FU). Likewise, drugs like cyclophosphamide, daclizumab, and anti-GITR or anti-OX40 antibodies may be used to inhibit Tregs.

To trigger overexpression or transcription of stress signals, it is also contemplated that the chemotherapy and/or radiation for the patient may be done using a low-dose regimen, preferably in a metronomic fashion. For example, it is generally preferred that such treatment will use doses effective to affect at least one of protein expression, cell division, and cell cycle, preferably to induce apoptosis or at least to induce or increase the expression of stress-related genes (and particularly NKG2D ligands). Thus, in further contemplated aspects, such treatment will include low dose treatment using one or more chemotherapeutic agents. Most typically, low dose treatments will be at exposures that are equal or less than 70%, equal or less than 50%, equal or less than 40%, equal or less than 30%, equal or less than 20%, equal or less than 10%, or equal or less than 5% of the $LD_{50}$ or $IC_{50}$ for the chemotherapeutic agent. Additionally, where advantageous, such low-dose regimen may be performed in a metronomic manner as described, for example, in U.S. Pat. Nos. 7,758,891, 7,771,751, 7,780,984, 7,981,445, and 8,034,375.

With respect to the particular drug used in such low-dose regimen, it is contemplated that all chemotherapeutic agents are deemed suitable. Among other suitable drugs, kinase inhibitors, receptor agonists and antagonists, anti-metabolic, cytostatic and cytotoxic drugs are all contemplated herein. However, particularly preferred agents include those identified to interfere or inhibit a component of a pathway that drives growth or development of the tumor. Suitable drugs can be identified using pathway analysis on omics data as described in, for example, WO 2011/139345 and WO 2013/062505. Most notably, so achieved expression of stress-related genes in the tumor cells will result in surface presentation of NKG2D, NKP30, NKP44, and/or NKP46 ligands, which in turn activate NK cells to specifically destroy the tumor cells. Thus, it should be appreciated that low-dose chemotherapy may be employed as a trigger in tumor cells to express and display stress related proteins, which in turn will trigger NK-cell activation and/or NK-cell mediated tumor cell killing. Additionally, NK-cell mediated killing will be associated with release of intracellular tumor specific antigens, which is thought to further enhance the immune response.

Consequently, in view of the above considerations and examples below, the inventor also contemplates numerous methods of transfecting host cells with recombinant viruses (and/or DNA/RNA) in combination with non-host cells, and particularly a method of transfecting a virus (e.g., recombinant adenovirus) into an immune competent cell (e.g., dendritic cell) lacking a receptor (e.g., CXADR) for entry of the virus into the cell. As will be readily appreciated, such methods can be performed in vitro and in vivo and as such also represent a method of treating a patient using an immune therapy (e.g., to treat cancer or infection) using a recombinant virus (or DNA/RNA) and non-host cells. Viewed from a different perspective, the inventor contemplates a method of increasing expression of a recombinant antigen in a host cell using the recombinant virus (or DNA/RNA) and non-host cells as discussed above and shown below. As also discussed before, the recombinant virus may be used to infect patient (or non-patient) cells ex vivo or in vivo in the presence of the non-host cells. For example, the virus and non-host cells may be injected subcutaneously or intravenously, or may be administered intranasally or via inhalation to so infect the patient's cells, and especially antigen presenting cells. Alternatively, immune competent cells (e.g., NK cells, T cells, macrophages, dendritic cells, etc.) of the patient (or from an allogeneic source) may be infected in vitro and then transfused into the patient.

Examples

Figure 2:
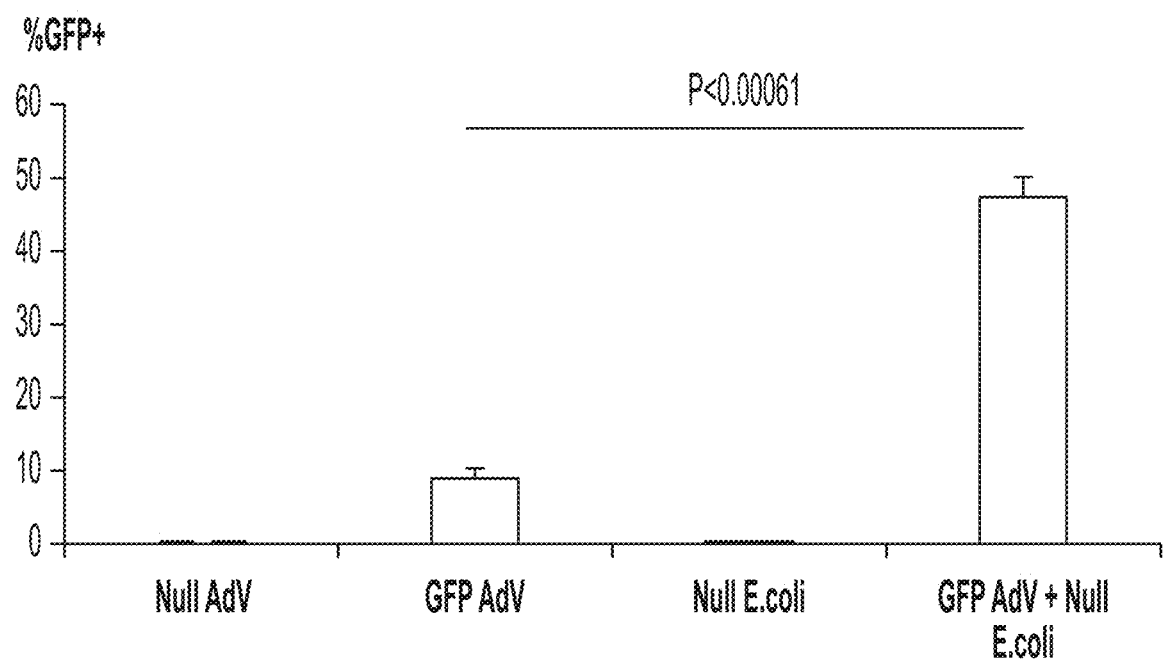
FIG. 2 is a graphical representation of the exemplary results of FIG. 1.

In a first series of experiments, the inventors used dendritic cells as host cells for a recombinant adenovirus AdV5 construct that included a sequence portion encoding GFP (green fluorescent protein). An *E. coli* Clearcoli BL21 strain (commercially available from Lucigen Corp., 2905 Parmenter St, Middleton, WI 53562, USA) was used as the non-host cell adjuvant at different ratios relative to the dendritic cells. After co-incubation (using appropriate controls), the dendritic cells were analyzed for expression of GFP and exemplary results for three samples are shown in FIG. 1. As can be readily seen from the graphs (top row, DC), dendritic cells per se had substantially no measureable fluorescence attributable to GFP. Where the dendritic cells were incubated with the recombinant adenovirus AdV5 construct (second row, +AdV-GFP), some fluorescence was observed. Viral entry of the recombinant adenovirus AdV5 construct into the dendritic cells is presumably via endocytosis or other mechanism that is independent of CXADR. Addition of *E. coli* Clearcoli BL21 to the dendritic cells in the absence of the recombinant adenovirus AdV5 construct (third row, +*E. coli*) resulted once more in no measurable substantial fluorescence. In contrast, where the recombinant adenovirus AdV5 construct was co-incubated with *E. coli* Clearcoli BL21, a significant and substantial increase in uptake and expression was observed (fourth row, +AdV-GFP & *E. coli*). Statistical analysis of the results of the above experiments is depicted in the graph of FIG. 2.

In vitro culture of human monocyte-derived dendritic cells. Human monocyte-derived dendritic cells (MoDC) were generated in vitro with a combination of recombinant human GM-CSF (200 U/ml) and recombinant human IL-4 (100 U/ml) for 72-96 h (Ref. Sieling, et al Evidence for Human CD4+ T Cells in the CD1-Restricted Repertoire: Derivation of Mycobacteria-Reactive T Cells from Leprosy Lesions J Immunol 2000 164 4790). Cells were harvested using incubation in PBS/EDTA (0.5 mM) to detach adherent cells and analyzed for CD1 expression by flow cytometry. MoDC were infected with Adv5 containing GFP at a multiplicity of infection (MOI) of 1000 to 1 (virus to MoDC)

and cultured for 24 h to allow infection and gene expression to take place. In some cases, *E. coli* Clearcoli BL21 (MOI=800) were added to the culture at the same time as Adv. After the 24 h culture, cells were harvested using PBS/EDTA and GFP expression evaluated using flow cytometry. Cultures were prepared in three replicates to establish an average value. Student's t test was applied to determine the significance of the difference between groups ($p<0.05$).

Figure 3:
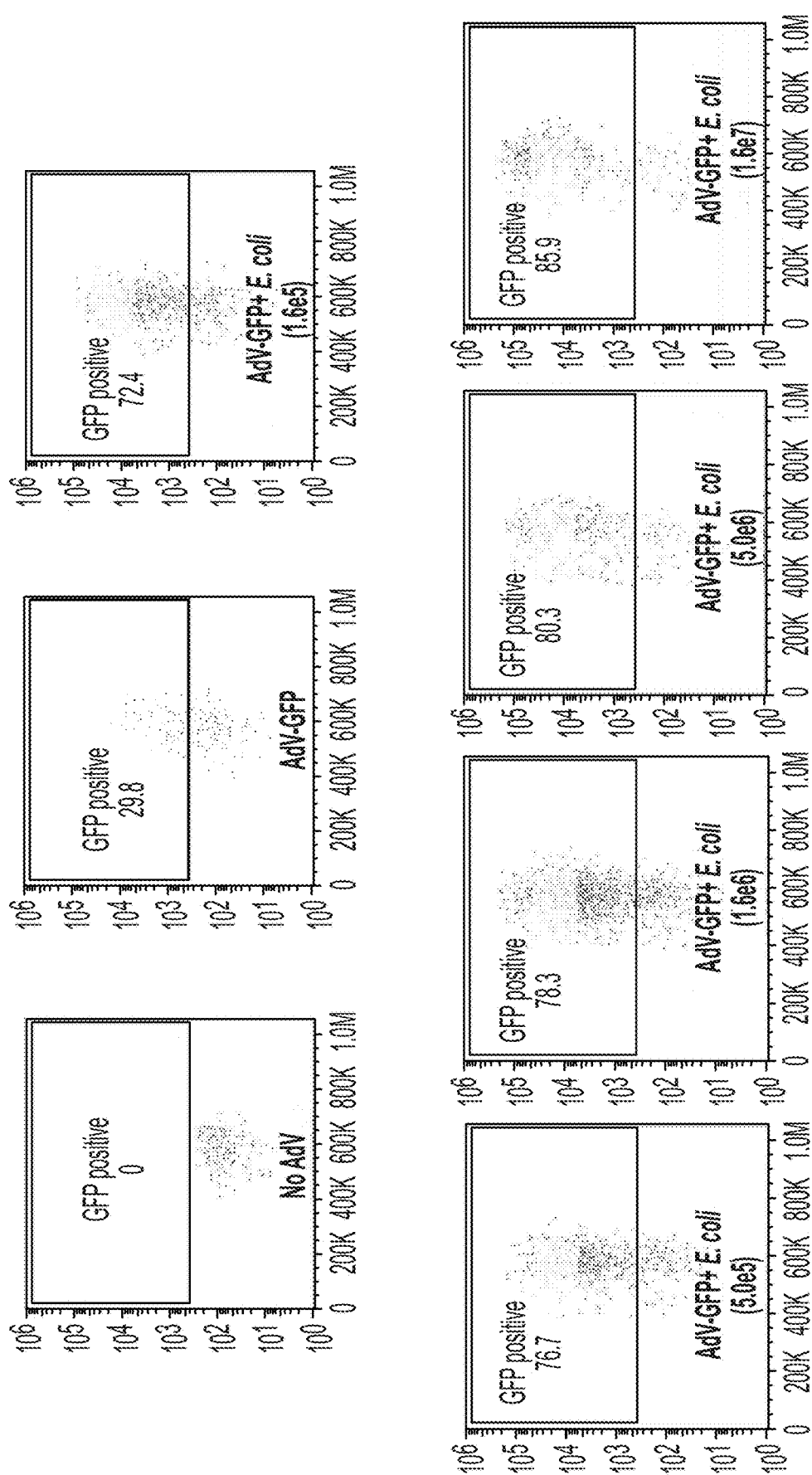
FIG. 3 depicts exemplary results for expression of a recombinant adenoviral payload at varying amounts of ΔLPS-*E. coli* adjuvant.
Figure 3:
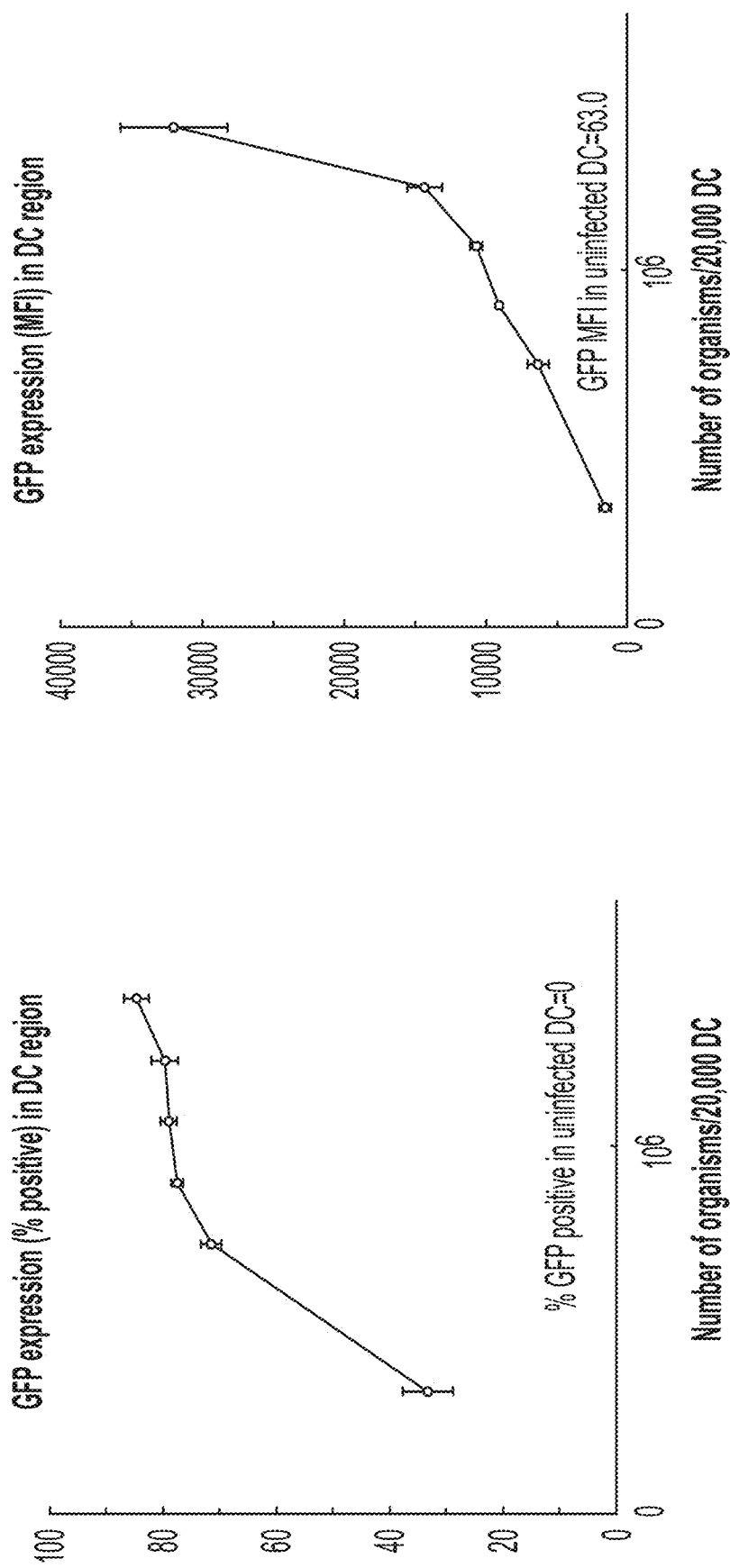

Using a substantially similar experimental approach, a more detailed analysis is shown in FIG. 3, where different ratios of dendritic cells and *E. coli* were used to determine the infectivity and expression strength. As can be readily seen from the results, absence of the recombinant adenovirus AdV5 construct (No AdV) resulted in 0% fluorescence positive dendritic cells. Without *E. coli*, but with recombinant adenovirus AdV5 construct, 29.8% of the dendritic cells showed fluorescence. Notably, in the presence of *E. coli* as adjuvant in escalating quantities over two logarithmic units (1.6e5→1.6e7), fluorescence dramatically increased (72.4%→85.9%). Such increase is unexpected and substantial. The graph (bottom left) of FIG. 3 illustrates the increase in transfection as a function of *E. coli* cells per 20,000 dendritic cells. Even more surprising was the finding that not only infection rates were substantially higher at increasing *E. coli* count, but that also the strength of expression of the recombinant GFP as measured by mean fluorescence intensity in the DC region dramatically increased as is shown in the graph (bottom right). Such findings are particularly surprising as dendritic cells lack CXADR and as increased uptake through other mechanisms would suggest increased protein degradation (i.e., decreased GFP).

Monocyte-derived dendritic cells were prepared as described above. MoDC ($2 \times 10^5$) were infected with Adv5 expressing GFP (MOI-1000) and remained in culture for 24 h. *E. coli* Clearcoli BL21 were added at increasing amounts ($1.6 \times 10^5$ to $1.6 \times 10^7$) during the 24 h infection with Adv to determine whether the presence of *E. coli* enhanced the level of GFP expression. After the 24 h culture, cells were harvested using PBS/EDTA and GFP expression evaluated using flow cytometry. Cultures were prepared in three replicates to establish an average value. Student's t test was applied to determine the significance of the difference between groups ($p<0.05$).

Figure 4:
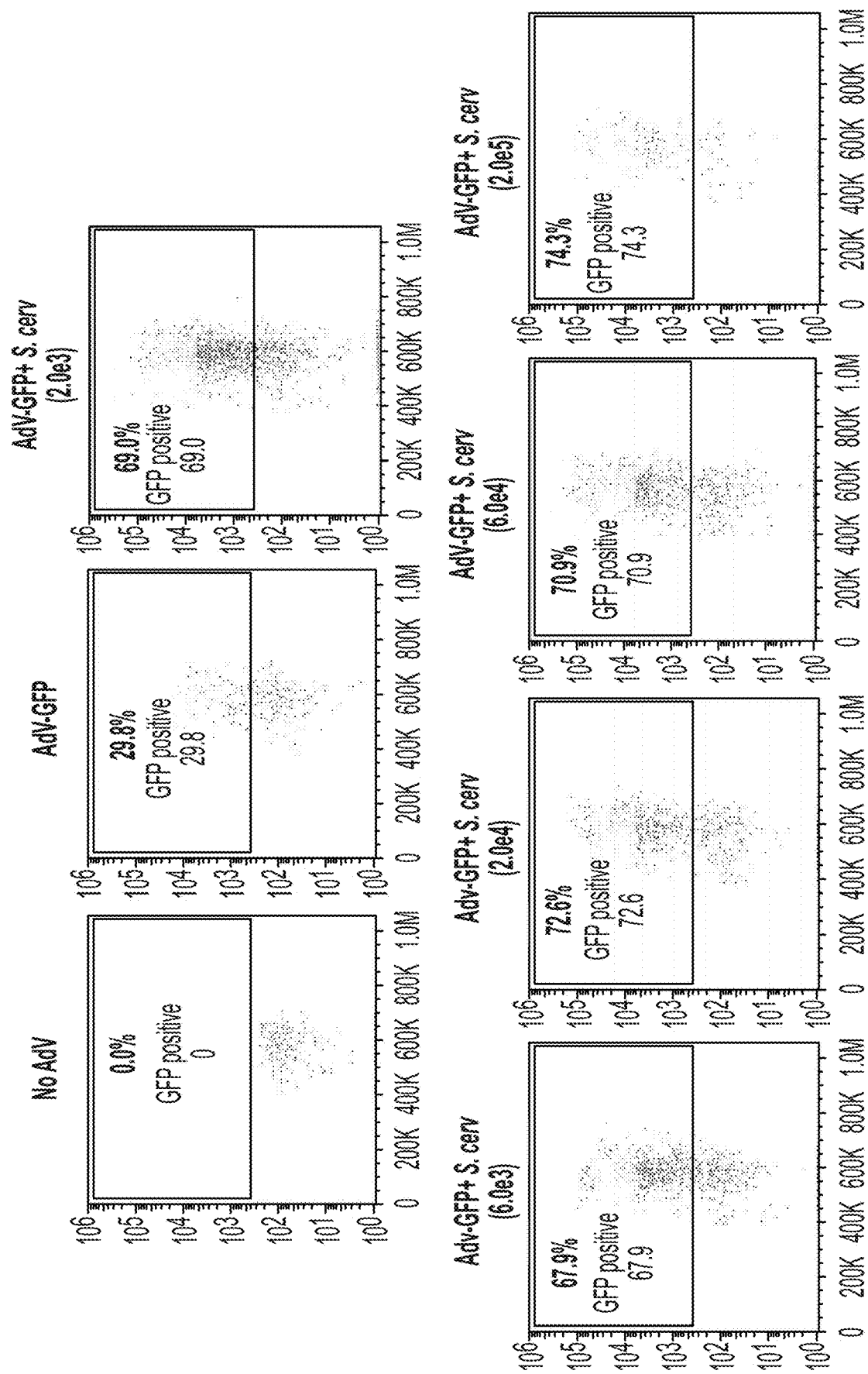
FIG. 4 depicts exemplary results for expression of a recombinant adenoviral payload at varying amounts of a *S. cerevisiae* adjuvant.
Figure 4:
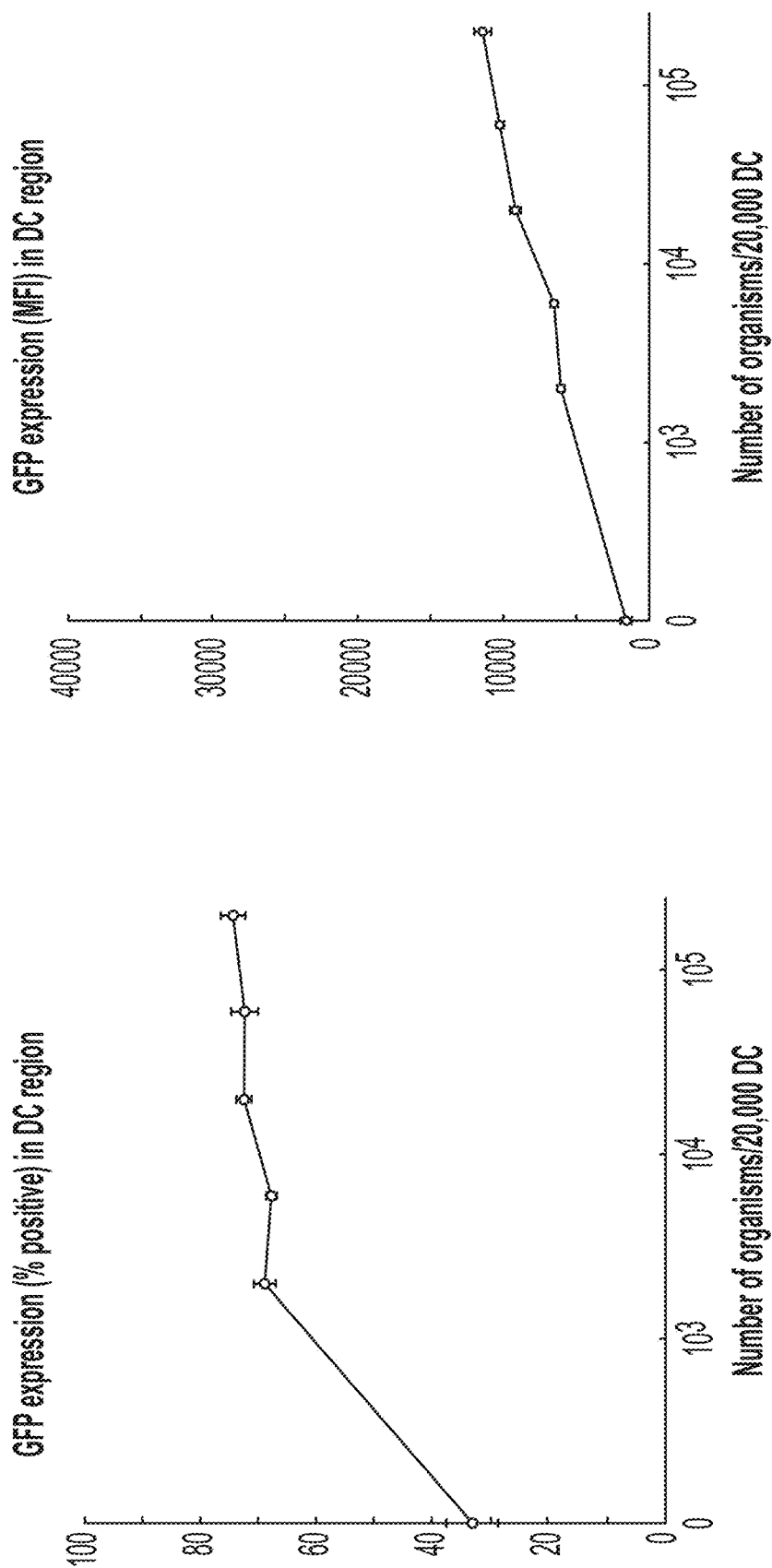

To confirm that such increase in uptake and expressivity can also be achieved using non-host cells other than *E. coli*, the inventor performed a series of experiments substantially similar to those of FIG. 3, but with *S. cerevisiae* as non-host cell. Exemplary results are shown in FIG. 4. As can be readily seen from the results, absence of the recombinant adenovirus AdV5 construct (No AdV) resulted in 0% fluorescence positive dendritic cells. Without *S. cerevisiae*, but with recombinant adenovirus AdV5 construct, 29.8% of the dendritic cells showed fluorescence. Notably, in the presence of *S. cerevisiae* as adjuvant in escalating quantities over two logarithmic units (2.0e3→2.0c5), fluorescence dramatically increased in all experiments, but not in a linear fashion (74.3%→69.0%). Once more, such increase is unexpected and substantial. The graph (bottom left) of FIG. 4 illustrates the increase in transfection as a function of *S. cerevisiae* cells per 20,000 dendritic cells. Similarly to *E. coli*, the strength of expression of the recombinant GFP as measured by mean fluorescence intensity in the DC region significantly increased as is shown in the graph (bottom right).

Monocyte-derived dendritic cells were prepared as described above. MoDC ($2 \times 10^5$) were infected with Adv5 expressing GFP (MOI-1000) and remained in culture for 24 h. *Saccharomyces cerevisiae* were added at increasing amounts ($2.0 \times 10^3$ to $2.0 \times 10^5$) during the 24 h infection with Adv to determine whether the presence of *S. cerv.* enhanced the level of GFP expression. After the 24 h culture, cells were harvested using PBS/EDTA and GFP expression evaluated using flow cytometry. Cultures were prepared in three replicates to establish an average value. Student's t test was applied to determine the significance of the difference between groups ($p<0.05$).

Figure 5:
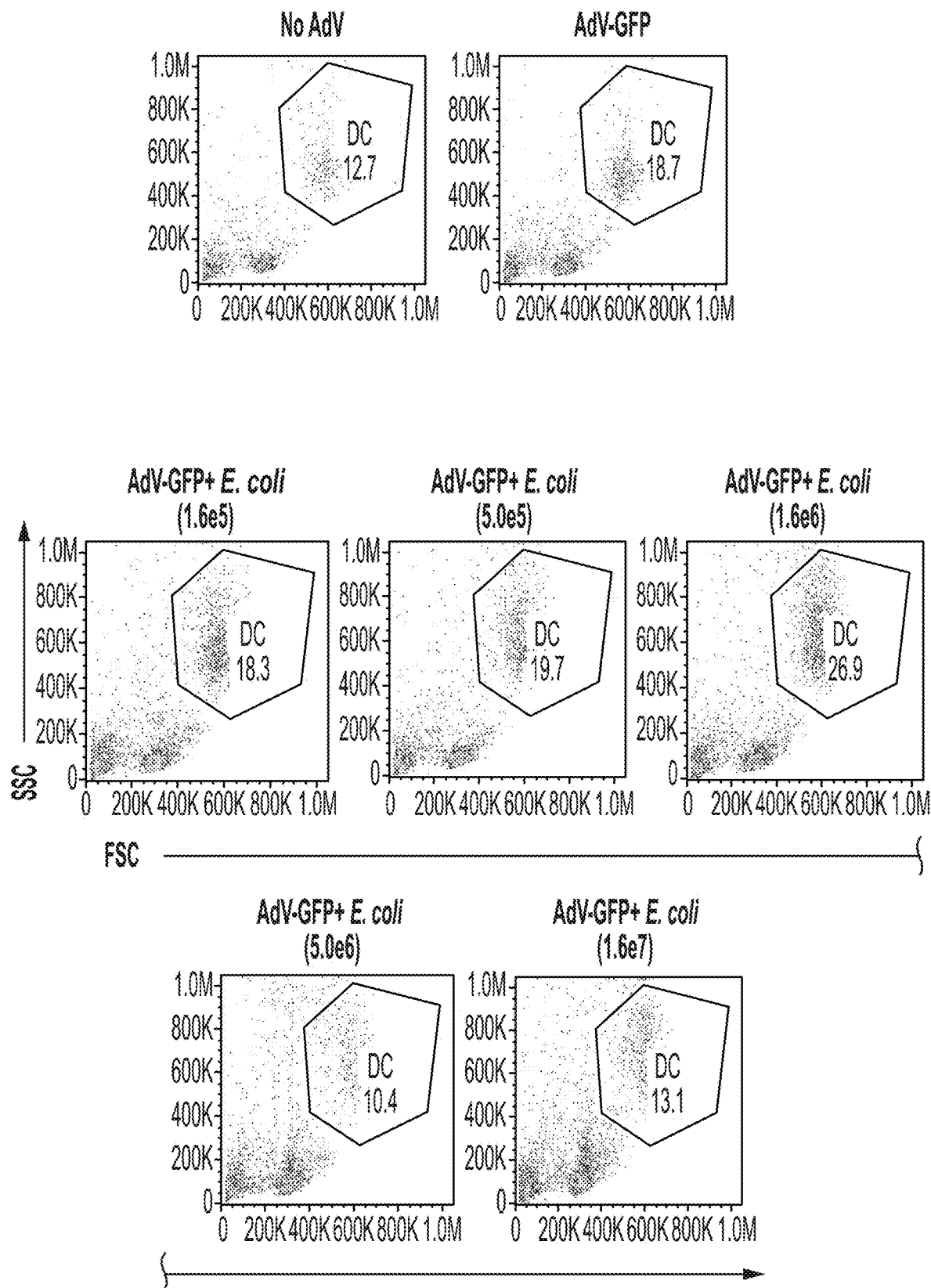
FIG. 5 depicts exemplary results for expression of a recombinant adenoviral payload at varying amounts of ΔLPS-*E. coli* adjuvant.
Figure 6:
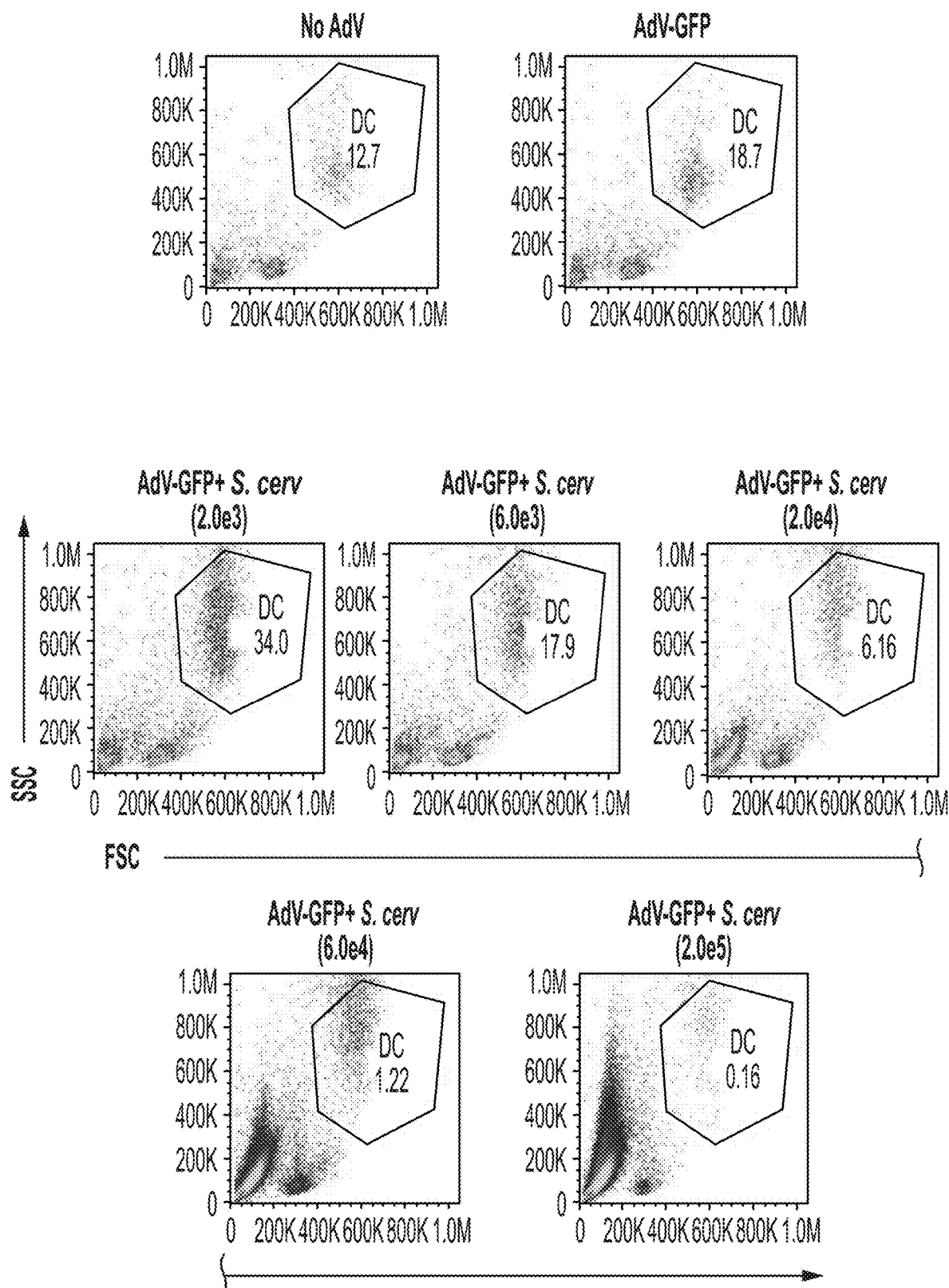
FIG. 6 depicts exemplary results for expression of a recombinant adenoviral payload at varying amounts of a *S. cerevisiae* adjuvant.

FIGS. 5 and 6 depict FACS scans of the dendritic cells in combination with the recombinant adenovirus AdV5 construct in ratios as described in FIGS. 3 and 4. These data are not a direct measure of viability, but are an approximation. For example, in FIG. 6 (*S. cerv* plus Adv-GFP), the % of cells in the enclosed region steadily decreases from 34% to 0.16% as the *S. cerv* increases. At the same time, a region in the lower left portion of the dot plot increases. The events in the lower left are indicative of dead cells. MoDC infected with Adv-GFP (MOI=1000) in the presence or absence of *E. coli* Clearcoli BL21 ($1.6 \times 10^5$ to $1.6 \times 10^7$) were evaluated by flow cytometry. Dot plots show representative (1 of 3) forward (cell size) and side (intracellular particles) scatter properties.

Figure 7:
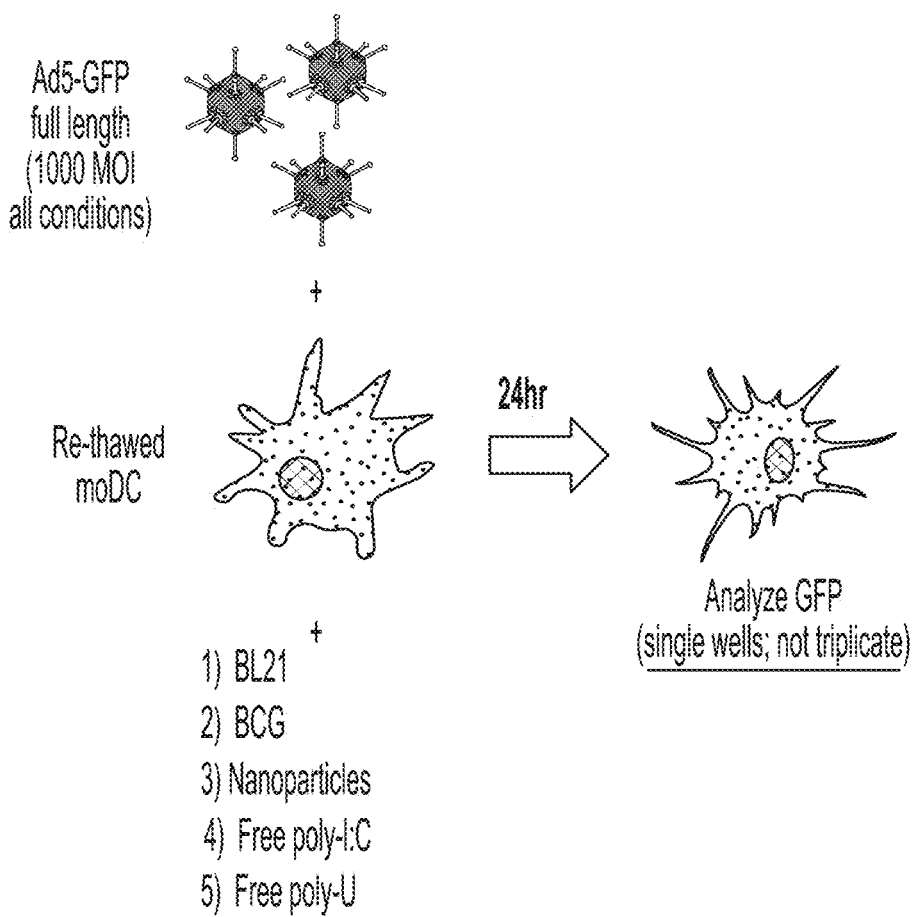
FIG. 7 depicts an exemplary work flow for experiments according to the inventive subject matter.

In still further examples, the inventors examined adjuvant compositions other than those described above, and an exemplary work flow is depicted in FIG. 7. Briefly, human monocyte-derived dendritic cells (MoDC) were generated and infected with a recombinant AdV5 virus that encoded GFP at 1000 MOI in the presence of the various adjuvants as indicated (*E. coli* BL21, BCG (Bacille Calmette Guerin, attenuated), non-targeting nanoparticles, polyI:C, and polyU). After incubation for 24 hours, green fluorescence was measured and cell viability determined.

Figure 8:
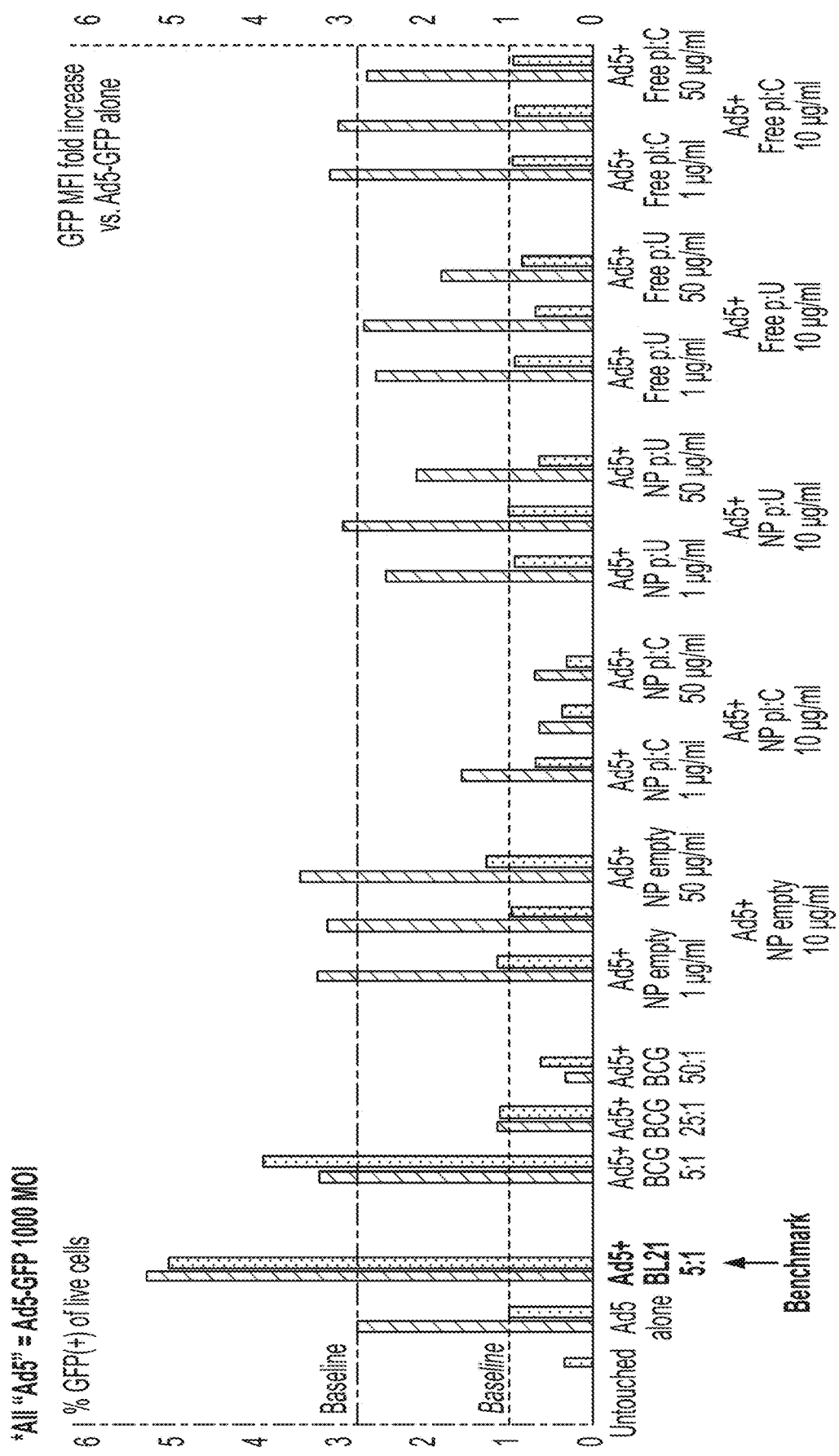
FIG. 8 depicts exemplary results for experiments of FIG. 7 using various adjuvants.
Figure 9:
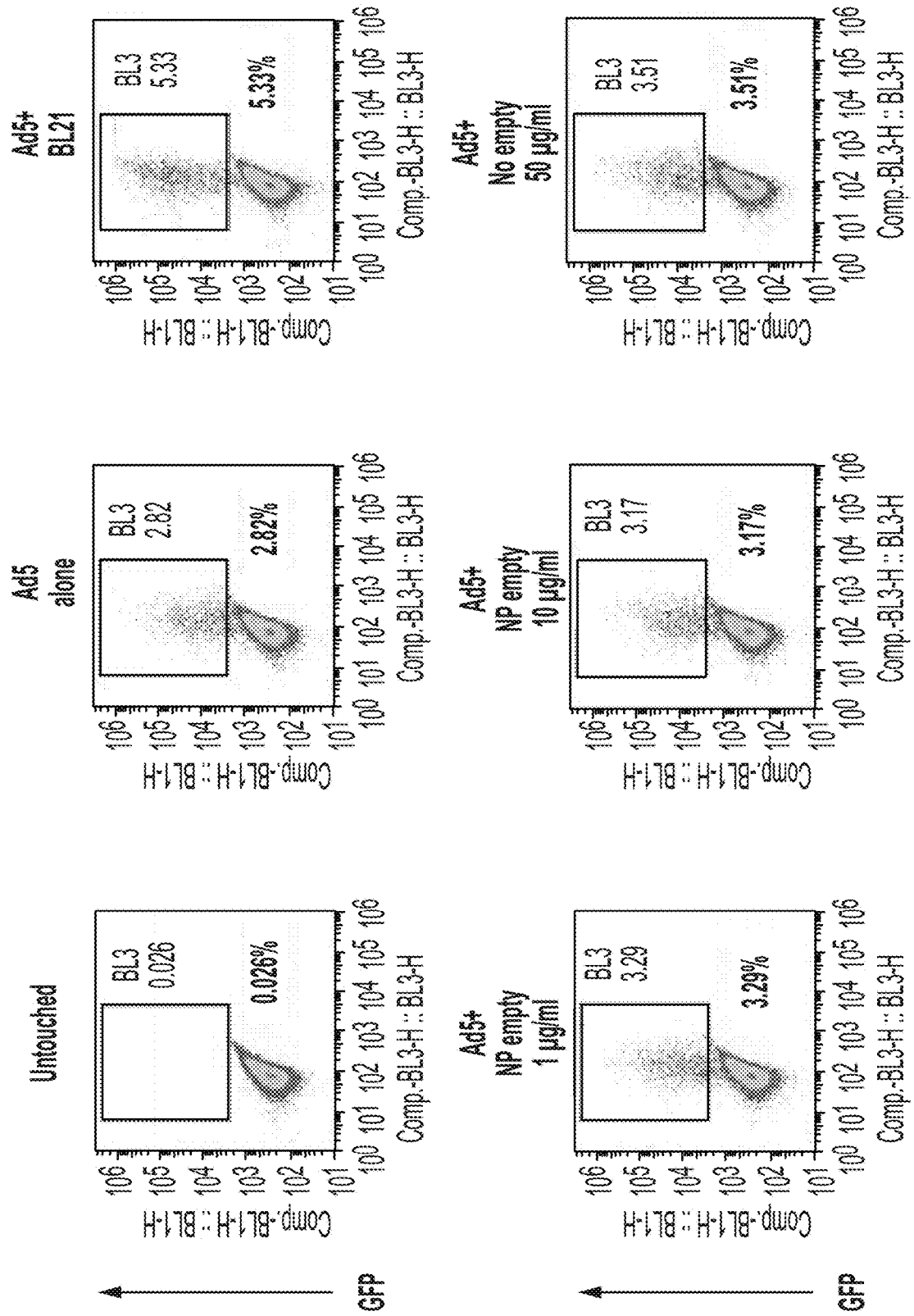
FIG. 9 depicts exemplary FACS results for experiments of FIG. 7 using various adjuvants.
Figure 9:
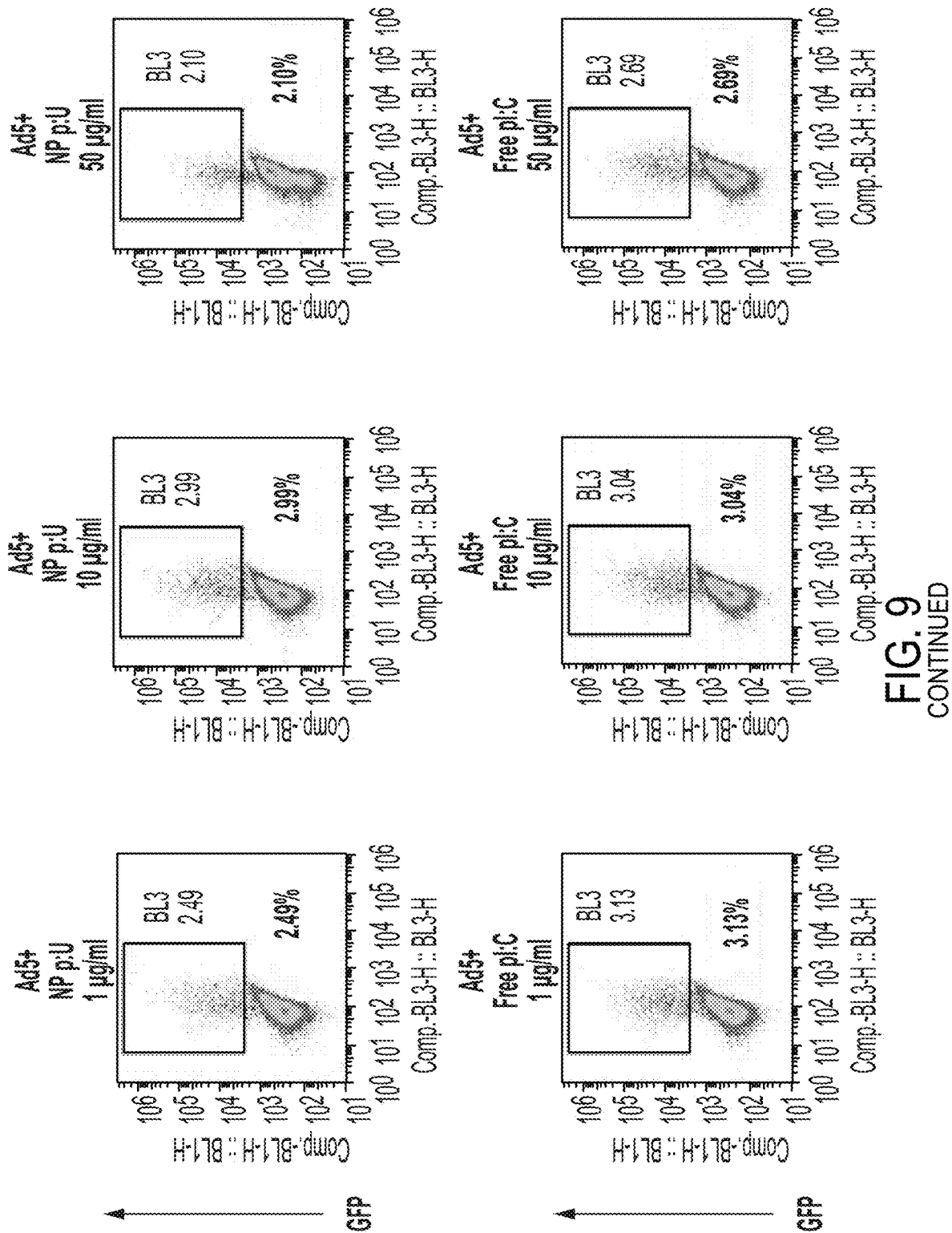
Figure 9:
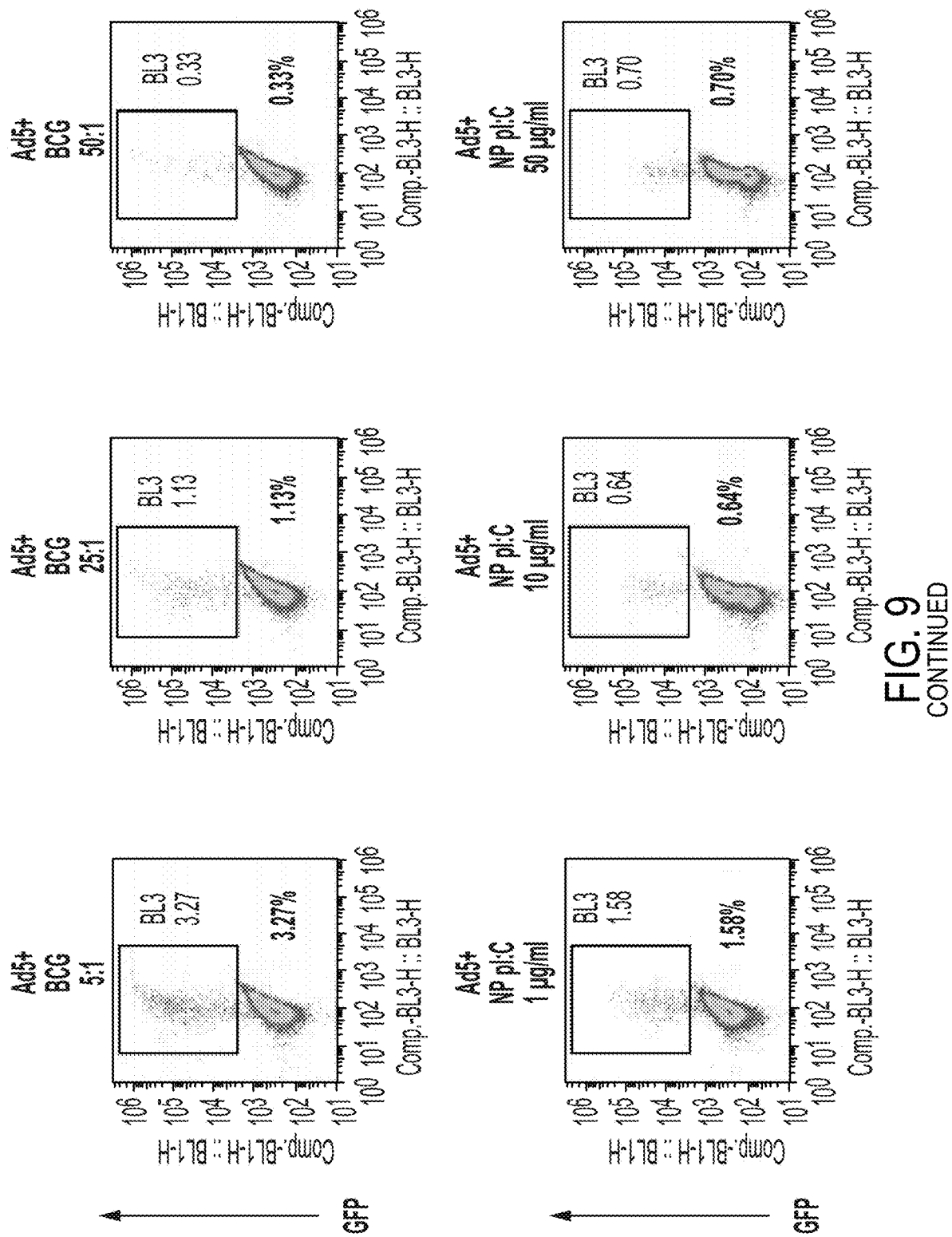
Figure 9:
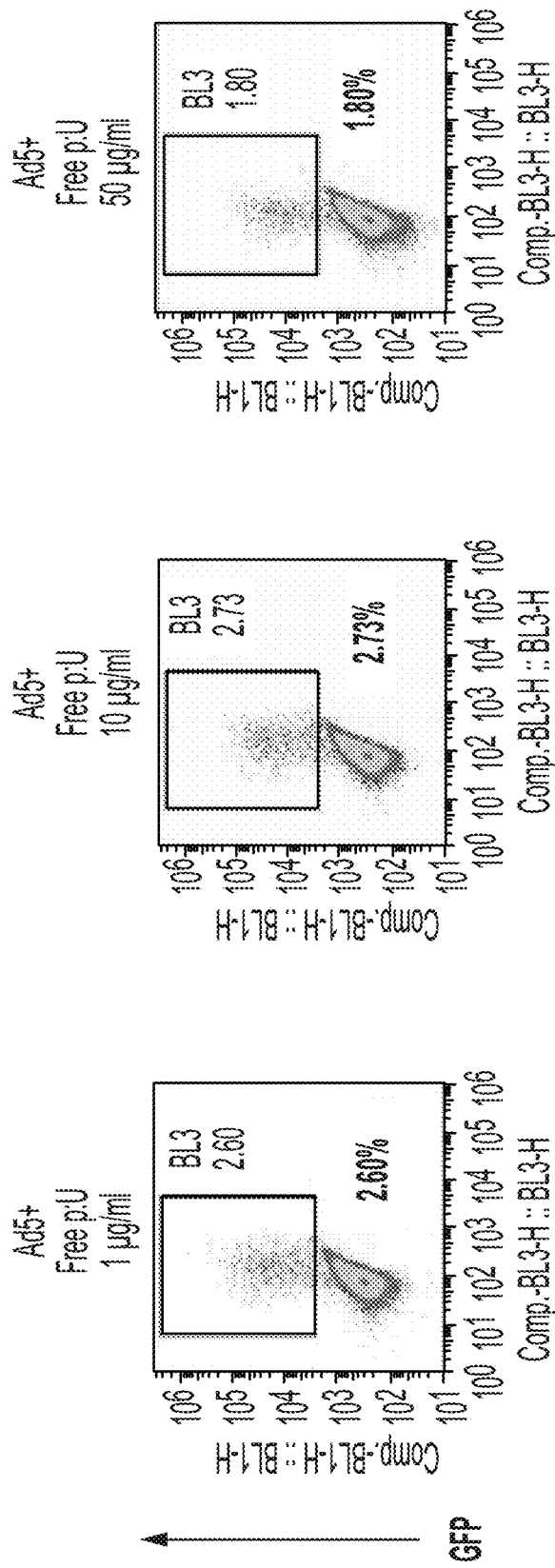
Figure 10:
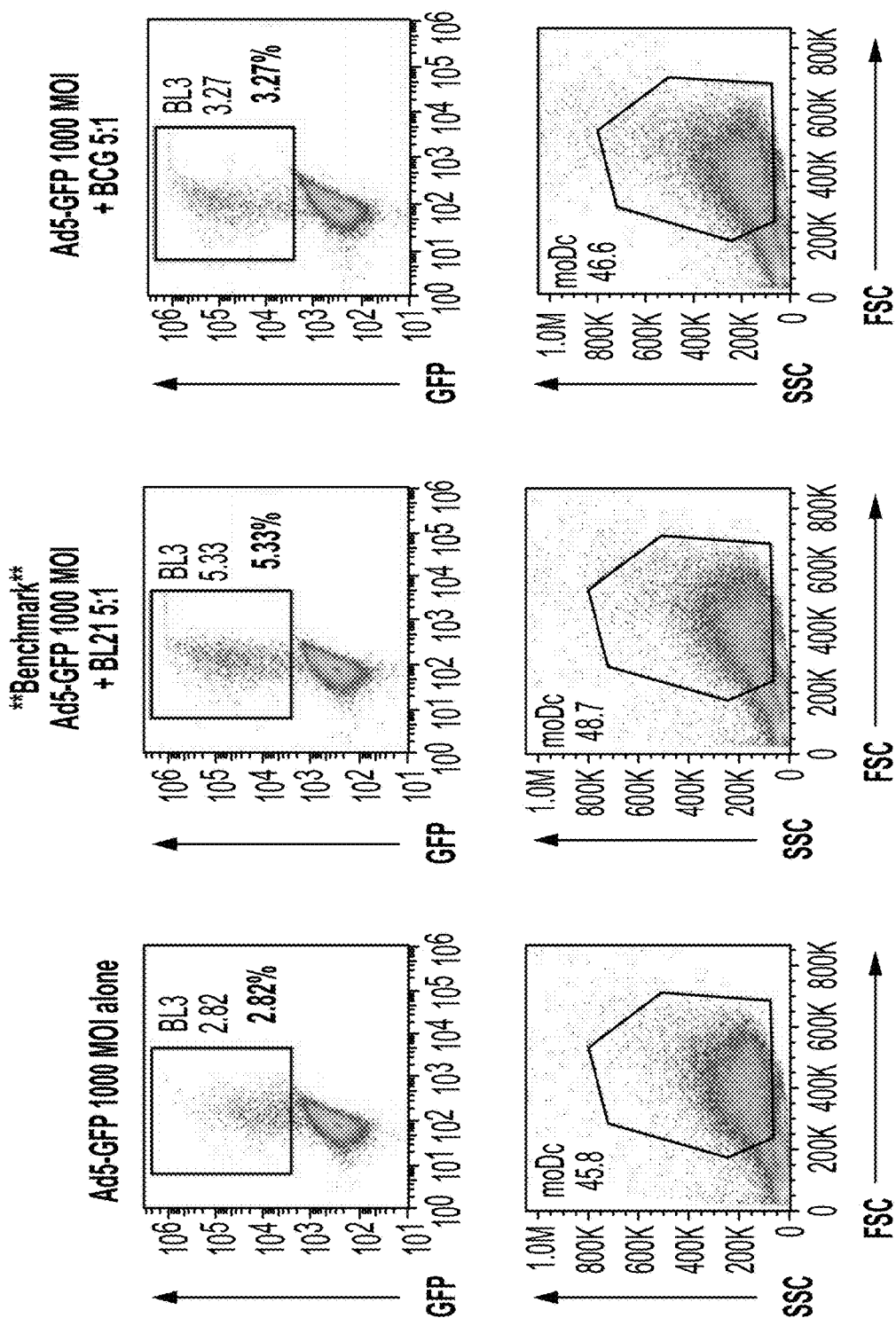
FIG. 10 depicts exemplary results indicating possible toxicity for the BCG adjuvant.
Figure 10:
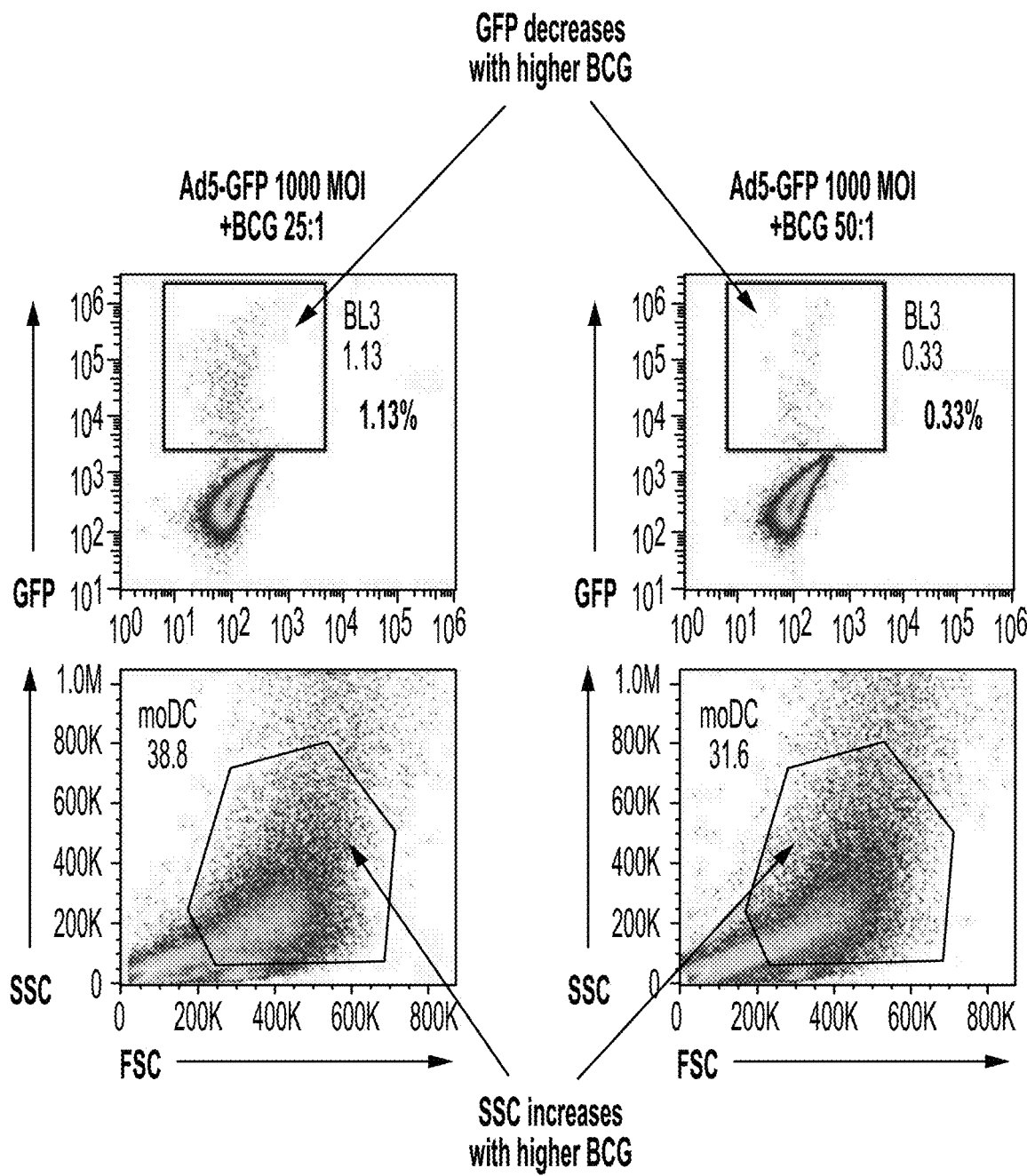

As can be seen from FIG. 8, *E. coli* was a particularly successful adjuvant with respect to both transfection activity and viability of the transfected cells. Notably, while BCG was effective both with regard to transfection activity and viability at low concentrations, higher concentrations appeared to reduce transfection and viability. Similarly, isolated TLR ligands (polyI:C, and polyU) and nanoparticles with or without pU/pI:C had little effect across all ratios tested as compared to ADV control alone. FIG. 9 illustrates exemplary FACS results for these experimental conditions as shown above each run. Once more lower concentrations of BCG had a significant stimulatory effect. To investigate further into BCG as a potential adjuvant with toxicity at high concentrations, the inventors ran further FACS studies that established potential toxicity as can be seen in FIG. 10. Thus, it should be noted that BL21 (empty vector) produced highest % GFP-expression and MFI in DCs transduced with Ad5-GFP, and that BCG may be toxic at MOIs above 5:1, resulting in decreased Ad5-GFP transduction efficiency (GFP expression).

Figure 11:
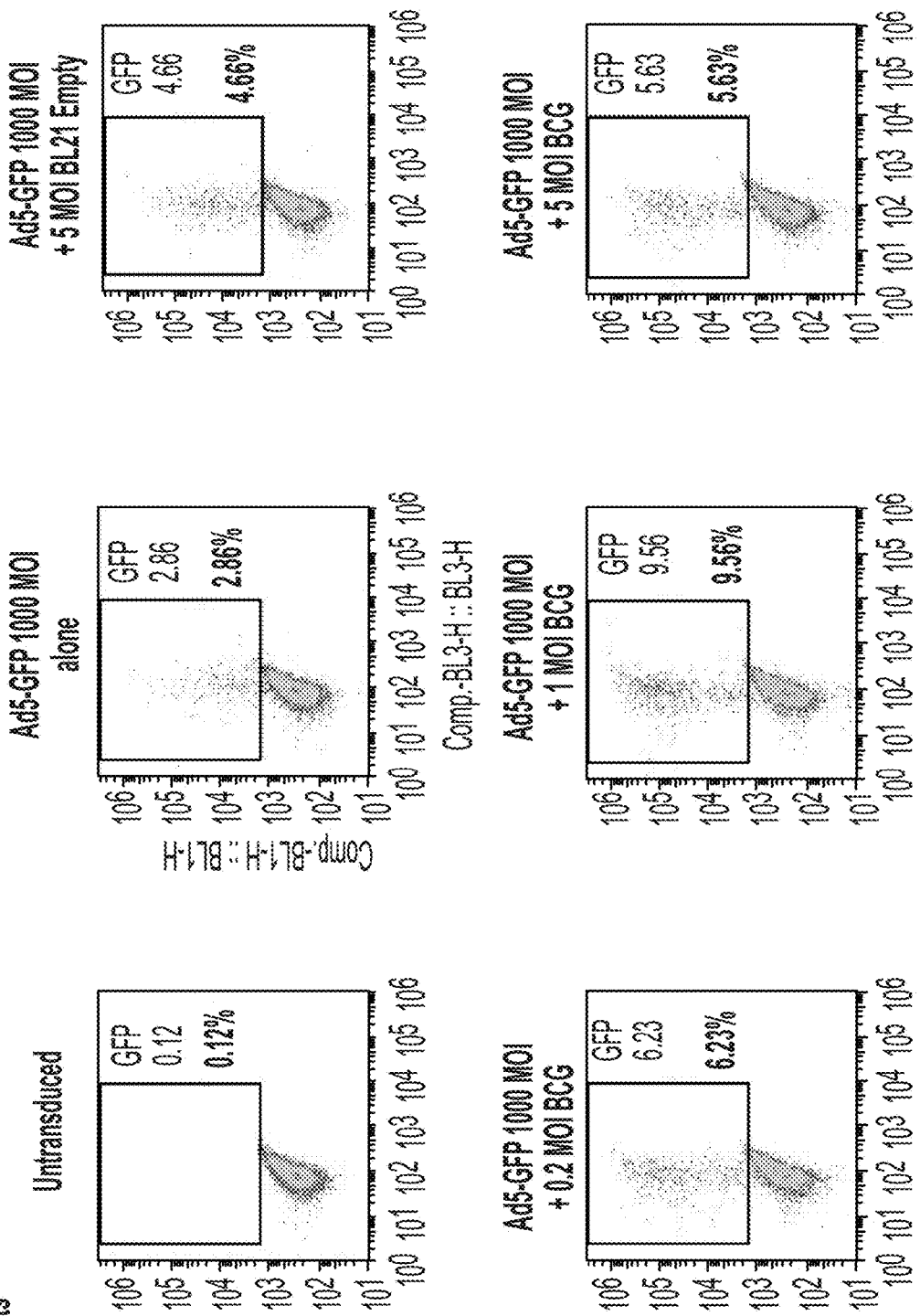
FIG. 11 depicts exemplary results for low dose BCG adjuvant.
Figure 12:
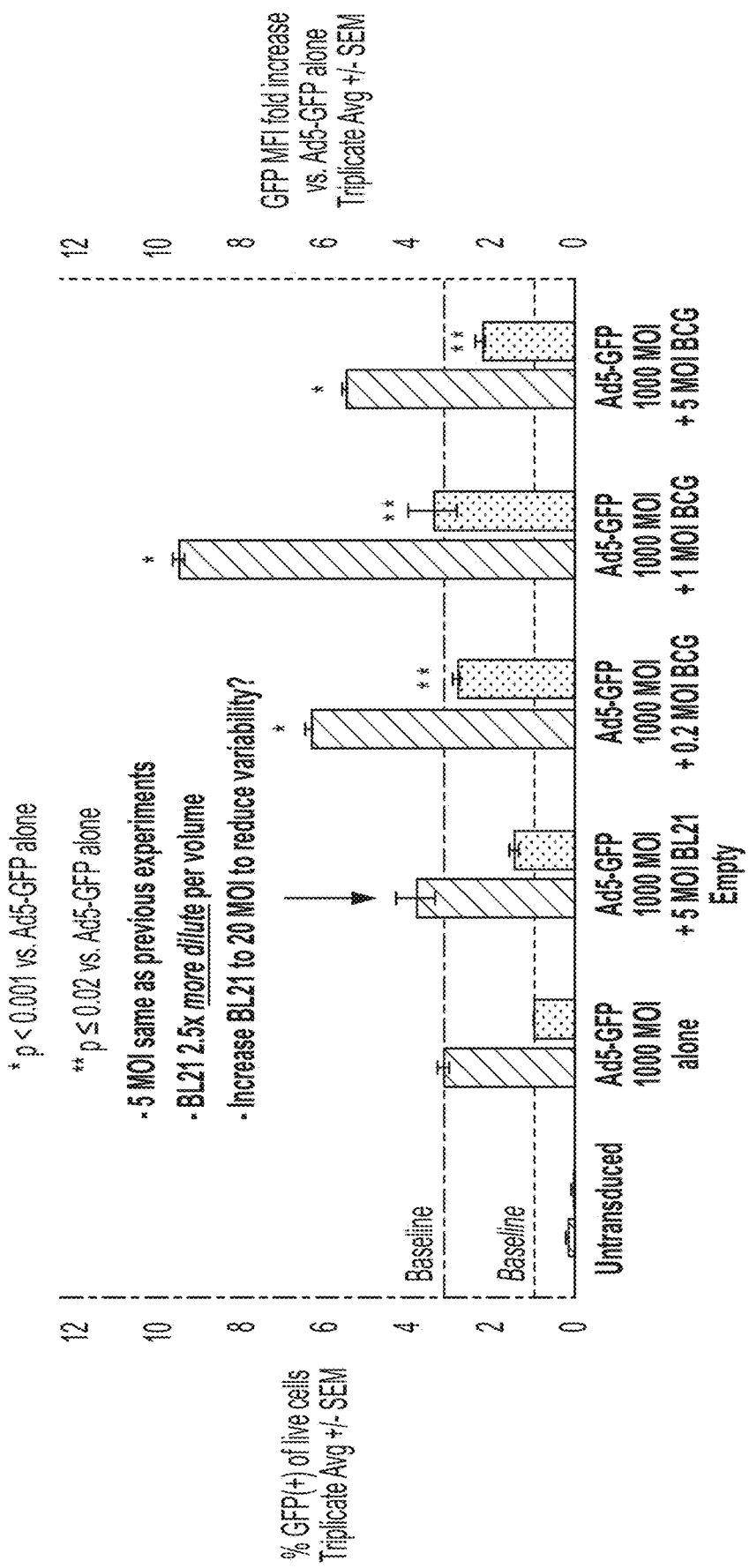
FIG. 12 depicts further exemplary results for low dose BCG adjuvant.

To evaluate BCG efficacy at lower concentrations, the inventors then tested BCG at low MOIs as is shown in FIG. 11. Unexpectedly, as can be readily seen from the FACS results, a low MOI for BCG had a superior effect even when compared to *E. coli*. Advantageously, the adjuvant effect of low dose BCG did not adversely affect the expression levels as can be seen from FIG. 12.

Thus, it should be appreciated that cell based adjuvants exhibited superior effects over nanoparticle or individual TLR ligand stimulation. As such, it is contemplated that live cells or attenuated cells, or irradiated (or otherwise killed) cells may provide a synergistic combination of known or unknown components that stimulate uptake and/or expression of recombinant DNA in viral vectors or other recombinant systems (e.g., recombinant bacterial or yeast). Such finding is particularly notable as adjuvants would be expected to increase degradation and processing and immune presentation of all components in a vaccine, which could lead to destruction of a recombinant payload. However, in contrast, the cellular adjuvants presented herein increased update and expression of the recombinant payload. As such, contemplated compositions and methods lend themselves to improved vaccine formulations, and especially recombinant viral, bacterial, and yeast vaccine compositions.

As used herein, the term "administering" a pharmaceutical composition or drug refers to both direct and indirect administration of the pharmaceutical composition or drug, wherein direct administration of the pharmaceutical composition or drug is typically performed by a health care professional (e.g., physician, nurse, etc.), and wherein indirect administration includes a step of providing or making available the pharmaceutical composition or drug to the health care professional for direct administration (e.g., via injection, infusion, oral delivery, topical delivery, etc.). Most preferably, the recombinant virus is administered via subcutaneous or subdermal injection. However, in other contemplated aspects, administration may also be intravenous injection. Alternatively, or additionally, antigen presenting cells may be isolated or grown from cells of the patient, infected in vitro, and then transfused to the patient. Therefore, it should be appreciated that contemplated systems and methods can be considered a complete drug discovery system (e.g., drug discovery, treatment protocol, validation, etc.) for highly personalized cancer treatment.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of treating a patient using an immune therapy, comprising:

administering a two-component vaccine formulation to the patient, wherein the vaccine formulation has an adjuvant component and a therapeutic component;

wherein the therapeutic component comprises an adenovirus having a genome that includes a recombinant sequence encoding an antigen, wherein the sequence is operably linked to a promoter to drive expression of the antigen in a cell of a patient;

wherein the adjuvant component comprises a *Bacillus* Calmette-Guérin (BCG) non-host cell; and wherein the BCG non-host cell is provided at a multiplicity of infection (MOI) of less than 5.

2. The method of claim 1, wherein the patient is treated to treat a cancer or an infection.

3. The method of claim 1, wherein the adjuvant component and the therapeutic component are co-administered to the patient.

4. The method of claim 1, wherein the two-component vaccine formulation comprises host cells from the patient, and wherein the host cells are infected with the adenovirus.

5. The method of claim 4, wherein the host cells from the patient comprise dendritic cells, macrophages, T cells, B cells, and/or monocytes.

6. The method of claim 1, wherein the therapeutic component has between $10^7$-$10^{10}$ adenoviral particles.

7. The method of claim 1, wherein the adenovirus has an E1 gene deletion and an E3 gene deletion.

8. The method of claim 7, wherein the adenovirus further has an E2b gene deletion.

9. The method of claim 1, wherein the recombinant sequence encodes a bacterial antigen, a viral antigen, a tumor associated antigen, and/or a patient- and tumor-specific neoepitope.

10. The method of claim 9, wherein the bacterial antigen, the viral antigen, the tumor associated antigen, and/or the patient- and tumor specific neoepitope is modified to direct the bacterial antigen, the viral antigen, the tumor associated antigen, and/or the patient- and tumor-specific neoepitope towards MHC-I and/or MHC-II presentation.

11. The method of claim 9, wherein the patient- and tumor-specific neoepitope has a length of between 8-20 amino acids.

12. The method of claim 1, wherein the recombinant sequence encodes multiple tumor associated antigens and/or patient- and tumor-specific neoepitopes arranged as a polytope.

13. The method of claim 1, wherein the recombinant sequence further include a sequence that encodes a co-stimulatory molecule.

14. The method of claim 13, wherein the co-stimulatory molecule is selected from the group consisting of CD80, CD86, CD30, CD40, CD30L, CD40L, CD54, CD11, ICOS-L, B7-H3, B7-H4, CD70, OX40L, 4-1BBL, GITR-L, TIM-3, TIM-4, CD48, CD58, TL1A, ICAM-1, LFA3, and a member of the SLAM family.

15. The method of claim 1, wherein the recombinant sequence further include a sequence that encodes a cytokine or cytokine analogs.

16. The method of claim 15, wherein the cytokine or cytokine analogs comprises IL-2, IL-15, and/or ALT-803.

17. The method of claim 1, wherein the recombinant sequence further include a sequence that encodes a peptide ligand that binds to a checkpoint receptor.

18. The method of claim 1, wherein the BCG non-host cell is provided at a multiplicity of infection (MOI) of about 1.0 to 0.2.

* * * * *